US009592083B2

(12) United States Patent
Walsh et al.

(10) Patent No.: US 9,592,083 B2
(45) Date of Patent: Mar. 14, 2017

(54) SPINE STABILIZATION DEVICE

(71) Applicant: New South Innovations Pty Limited, Sydney (AU)

(72) Inventors: William Robert Walsh, Maroubra (AU); Matthew Henry Pelletier, Maroubra (AU)

(73) Assignee: NEW SOUTH INNOVATIONS PTY LIMITED, Sydney (AU)

( * ) Notice: Subject to any disclaimer, the term of this patent is extended or adjusted under 35 U.S.C. 154(b) by 48 days.

(21) Appl. No.: 14/413,229

(22) PCT Filed: Feb. 28, 2014

(86) PCT No.: PCT/IB2014/000773
§ 371 (c)(1),
(2) Date: Jan. 6, 2015

(87) PCT Pub. No.: WO2015/028853
PCT Pub. Date: Mar. 5, 2015

(65) Prior Publication Data
US 2015/0374412 A1    Dec. 31, 2015

(30) Foreign Application Priority Data
Aug. 30, 2013  (WO) ............... PCT/AU2013/000984

(51) Int. Cl.
*A61B 17/70*  (2006.01)
*A61F 2/44*   (2006.01)
(Continued)

(52) U.S. Cl.
CPC ........ *A61B 17/707* (2013.01); *A61B 17/7062* (2013.01); *A61B 17/7065* (2013.01);
(Continued)

(58) Field of Classification Search
CPC ..................... A61B 17/7062; A61F 2/4405
(Continued)

(56) References Cited

U.S. PATENT DOCUMENTS 5,527,311 A   6/1996  Procter et al.
5,645,084 A   7/1997  McKay
(Continued)

FOREIGN PATENT DOCUMENTS

AU       769376 B2     1/2004
AU    2011203024 A1    7/2011
(Continued)

OTHER PUBLICATIONS

"Aesculap Implant Systems Launches PL-AGE® Anterior Cervical Fusion System," accessed at http://news.cision.com/aesculap/r/aesculap-implant-systems-launches-pl-age--anterior-cervical-fusion-system,c9382058 , Mar. 8, 2013, pp. 1-5.
(Continued)

*Primary Examiner* — Ellen C Hammond
*Assistant Examiner* — Stuart S Bray
(74) *Attorney, Agent, or Firm* — Turk IP Law, LLC

(57) ABSTRACT

Technologies are generally provided for devices, systems, and methods to provide spinal fixation, spinal stabilization, and/or spinal fusion. Example devices may include a first end and a second end with a middle portion extending between the first and second end. The first end may be configured to be in contact with a portion of a first or upper vertebra and the second end may be configured to be in contact with a portion of a second or lower vertebra in an adjacent vertebral pair. Portions of the vertebra which may be in contact with the device may include lamina, processes, vertebral bodies, and facet joints. The example devices may include bone engagement features, such as screws or similar fasteners, to enhance stabilization and fixation when in
(Continued)

contact with the vertebrae. Additionally, the devices may include a bone integration feature to promote bone growth and to facilitate fusion between the vertebrae.

17 Claims, 21 Drawing Sheets

(51) Int. Cl.
  *A61F 2/30* (2006.01)
  *A61B 17/56* (2006.01)
(52) U.S. Cl.
  CPC ............ *A61B 17/7067* (2013.01); *A61F 2/44* (2013.01); *A61F 2/4405* (2013.01); *A61F 2/4455* (2013.01); *A61B 2017/564* (2013.01); *A61F 2002/3082* (2013.01); *A61F 2002/30092* (2013.01); *A61F 2002/3093* (2013.01); *A61F 2002/30131* (2013.01); *A61F 2002/30136* (2013.01); *A61F 2002/30166* (2013.01); *A61F 2002/30181* (2013.01); *A61F 2002/30301* (2013.01); *A61F 2002/30565* (2013.01); *A61F 2002/30784* (2013.01); *A61F 2002/30971* (2013.01); *A61F 2310/00017* (2013.01); *A61F 2310/00023* (2013.01); *A61F 2310/00029* (2013.01); *A61F 2310/00131* (2013.01); *A61F 2310/00161* (2013.01); *A61F 2310/00329* (2013.01); *A61F 2310/00395* (2013.01); *A61F 2310/00796* (2013.01)
(58) Field of Classification Search
  USPC ......................................................... 606/249
  See application file for complete search history.

(56) References Cited

U.S. PATENT DOCUMENTS

| | | | |
|---|---|---|---|
| 5,782,919 A | 7/1998 | Zdeblick et al. | |
| 6,346,123 B1 | 2/2002 | McKay | |
| 6,547,795 B2 | 4/2003 | Schneiderman | |
| 6,565,571 B1 | 5/2003 | Jackowski et al. | |
| 6,585,769 B1 | 7/2003 | Muhanna et al. | |
| 6,626,944 B1 | 9/2003 | Taylor | |
| 6,719,795 B1 | 4/2004 | Cornwall et al. | |
| 7,261,738 B2 | 8/2007 | Casey | |
| 7,501,073 B2 | 3/2009 | Wen et al. | |
| 7,611,526 B2 | 11/2009 | Carl et al. | |
| 7,662,186 B2 | 2/2010 | Bagga et al. | |
| 7,666,208 B1 | 2/2010 | Asfora | |
| 7,722,647 B1 | 5/2010 | Wang et al. | |
| 7,722,895 B1 | 5/2010 | McKay et al. | |
| 7,780,709 B2* | 8/2010 | Bruneau | A61B 17/7062 606/246 |
| 7,789,898 B2 | 9/2010 | Peterman | |
| D643,927 S | 8/2011 | Prasad et al. | |
| 8,034,079 B2 | 10/2011 | Bruneau et al. | |
| 8,133,261 B2* | 3/2012 | Fisher | A61B 17/7064 606/247 |
| 8,197,513 B2 | 6/2012 | Fisher et al. | |
| 8,221,461 B2 | 7/2012 | Kuiper et al. | |
| 8,303,879 B2 | 11/2012 | Bertele et al. | |
| 8,308,771 B2 | 11/2012 | Bennett et al. | |
| 8,353,912 B2 | 1/2013 | Darian et al. | |
| 8,579,941 B2 | 11/2013 | Chervitz et al. | |
| 2001/0014831 A1 | 8/2001 | Scarborough | |
| 2004/0259972 A1* | 12/2004 | Ringeisen | A61B 17/68 523/113 |
| 2005/0080486 A1* | 4/2005 | Fallin | A61F 2/4405 623/17.11 |
| 2005/0131412 A1 | 6/2005 | Olevsky et al. | |
| 2005/0203512 A1* | 9/2005 | Hawkins | A61B 17/7062 606/249 |
| 2005/0203624 A1* | 9/2005 | Serhan | A61B 17/7062 623/17.11 |
| 2006/0113814 A1 | 6/2006 | Kunz | |
| 2006/0136060 A1* | 6/2006 | Taylor | A61B 17/7062 623/17.13 |
| 2006/0190081 A1 | 8/2006 | Kraus et al. | |
| 2006/0224159 A1* | 10/2006 | Anderson | A61B 17/7062 606/248 |
| 2006/0247634 A1* | 11/2006 | Warner | A61B 17/7062 606/249 |
| 2006/0247650 A1 | 11/2006 | Yerbs et al. | |
| 2006/0276788 A1 | 12/2006 | Berry et al. | |
| 2006/0293662 A1* | 12/2006 | Boyer, II | A61B 17/1671 606/249 |
| 2007/0016204 A1 | 1/2007 | Martinez et al. | |
| 2007/0049941 A1 | 3/2007 | Thramann | |
| 2007/0083266 A1 | 4/2007 | Lang | |
| 2007/0161990 A1 | 7/2007 | Hillyard et al. | |
| 2007/0179611 A1 | 8/2007 | DiPoto et al. | |
| 2007/0191833 A1* | 8/2007 | Bruneau | A61B 17/7062 606/86 A |
| 2007/0225812 A1 | 9/2007 | Gill | |
| 2007/0239278 A1 | 10/2007 | Heinz | |
| 2007/0270844 A1 | 11/2007 | Lin et al. | |
| 2007/0288014 A1 | 12/2007 | Shadduck et al. | |
| 2008/0021476 A1 | 1/2008 | Kirschman | |
| 2008/0091198 A1 | 4/2008 | Leibel et al. | |
| 2008/0114357 A1 | 5/2008 | Allard et al. | |
| 2008/0161810 A1 | 7/2008 | Melkent | |
| 2008/0177264 A1* | 7/2008 | Alamin | A61B 17/7062 606/74 |
| 2008/0215096 A1 | 9/2008 | Nash et al. | |
| 2008/0228225 A1* | 9/2008 | Trautwein | A61B 17/1606 606/246 |
| 2008/0234824 A1* | 9/2008 | Youssef | A61B 17/7062 623/17.16 |
| 2008/0281423 A1 | 11/2008 | Sheffer et al. | |
| 2008/0300685 A1 | 12/2008 | Carls et al. | |
| 2008/0306554 A1 | 12/2008 | Mckinley | |
| 2009/0005819 A1* | 1/2009 | Ben-Mokhtar | A61B 17/7062 606/249 |
| 2009/0054931 A1* | 2/2009 | Metz-Stavenhagen | A61B 17/7062 606/248 |
| 2009/0112326 A1* | 4/2009 | Lehuec | A61F 2/441 623/17.16 |
| 2009/0131986 A1 | 5/2009 | Lee et al. | |
| 2009/0163920 A1 | 6/2009 | Hochschuler et al. | |
| 2009/0163958 A1 | 6/2009 | Tarcha et al. | |
| 2009/0246244 A1 | 10/2009 | McKay et al. | |
| 2009/0248079 A1* | 10/2009 | Kwak | A61B 17/7062 606/249 |
| 2009/0264929 A1* | 10/2009 | Alamin | A61B 17/7062 606/248 |
| 2009/0292314 A1* | 11/2009 | Mangione | A61B 17/7062 606/249 |
| 2009/0306716 A1* | 12/2009 | Beger | A61B 17/7062 606/249 |
| 2010/0010548 A1* | 1/2010 | Hermida Ochoa | A61B 17/06066 606/86 A |
| 2010/0030269 A1* | 2/2010 | Taylor | A61B 17/7062 606/248 |
| 2010/0070038 A1* | 3/2010 | Taylor | A61B 17/7065 623/17.16 |
| 2010/0082067 A1 | 4/2010 | Kondrashov | |
| 2010/0094426 A1 | 4/2010 | Grohowski, Jr. et al. | |
| 2010/0121381 A1* | 5/2010 | Berta | A61B 17/7055 606/264 |
| 2010/0131008 A1* | 5/2010 | Overes | A61B 17/7062 606/247 |
| 2010/0152779 A1 | 6/2010 | Allard et al. | |
| 2010/0249840 A1* | 9/2010 | Tanaka | A61B 17/7062 606/249 |
| 2010/0312278 A1* | 12/2010 | Linares | A61B 17/7062 606/249 |

(56) References Cited

U.S. PATENT DOCUMENTS

| | | | |
|---|---|---|---|
| 2011/0029020 A1* | 2/2011 | Gordon | A61B 17/7062 606/248 |
| 2011/0040330 A1* | 2/2011 | Sheffer | A61B 17/7062 606/249 |
| 2011/0040383 A1* | 2/2011 | Wurfel | A61B 17/7065 623/17.11 |
| 2011/0106263 A1 | 5/2011 | Eisermann | |
| 2011/0172711 A1* | 7/2011 | Kirschman | A61B 17/7058 606/252 |
| 2011/0190818 A1* | 8/2011 | Douget | A61B 17/7062 606/249 |
| 2011/0208244 A1* | 8/2011 | Shin | A61B 17/7062 606/249 |
| 2011/0218572 A1 | 9/2011 | Lechmann et al. | |
| 2011/0307010 A1* | 12/2011 | Pradhan | A61B 17/7062 606/249 |
| 2012/0010662 A1 | 1/2012 | O'Neil et al. | |
| 2012/0016420 A1* | 1/2012 | Naraghi | A61B 17/7064 606/250 |
| 2012/0046749 A1 | 2/2012 | Tatsumi | |
| 2012/0065683 A1* | 3/2012 | Kuo | A61B 17/7062 606/248 |
| 2012/0109202 A1* | 5/2012 | Kretzer | A61B 17/7049 606/248 |
| 2012/0143337 A1 | 6/2012 | Jensen et al. | |
| 2012/0165872 A1* | 6/2012 | Alamin | A61B 17/7062 606/248 |
| 2012/0215260 A1* | 8/2012 | Paul | A61B 17/7053 606/249 |
| 2012/0265250 A1* | 10/2012 | Ali | A61B 17/7001 606/279 |
| 2012/0277801 A1* | 11/2012 | Marik | A61B 17/7064 606/279 |
| 2013/0144386 A1 | 6/2013 | Horton et al. | |
| 2013/0184751 A1* | 7/2013 | Siegfried | A61B 17/7068 606/248 |
| 2013/0184826 A1* | 7/2013 | Thaiyananthan | A61F 2/442 623/17.16 |
| 2013/0190820 A1 | 7/2013 | Siegfried et al. | |
| 2013/0211524 A1* | 8/2013 | Hugues | A61F 2/44 623/17.11 |
| 2013/0244942 A1 | 9/2013 | Benedict et al. | |
| 2013/0325068 A1* | 12/2013 | Fielding | A61B 17/7062 606/263 |
| 2013/0338720 A1 | 12/2013 | Kleiner | |
| 2014/0012326 A1* | 1/2014 | Alamin | A61B 17/7062 606/279 |
| 2014/0025114 A1* | 1/2014 | Kim | A61B 17/7062 606/249 |
| 2014/0032118 A1 | 1/2014 | Yarus et al. | |

FOREIGN PATENT DOCUMENTS

| | | |
|---|---|---|
| AU | 2013206209 A1 | 6/2013 |
| CN | 2782033 Y | 5/2006 |
| CN | 101444435 B | 12/2010 |
| CN | 201861801 U | 6/2011 |
| EP | 149540 A2 | 7/1985 |
| EP | 0532421 A1 | 3/1993 |
| EP | 701803 A1 | 3/1996 |
| EP | 1844798 A1 | 10/2007 |
| EP | 996385 B1 | 1/2008 |
| JP | 2005021420 A | 1/2005 |
| WO | 0003653 A2 | 1/2000 |
| WO | 2012006064 A1 | 1/2012 |

OTHER PUBLICATIONS

"Anterior Cervical Plate(cervical Spine Fixation System)," accessed at http://www.alibaba.com/product-detail/Anterior-cervical-plate-cervical-spine-fixation_614171434.html, accessed on Sep. 20, 2014, pp. 1-4.

"DTRAX, by Providence Medical Technology," accessed at https://web.archive.org/web/20131101022739/http://providencemt.com/procedure, accessed on Sep. 20, 2014, pp. 1-2.

"InterFuse S™ Interbody Fusion System," Surgical Technique Manual, MS 4043-02 Rev. O, accessed at http://www.vti-spine.com/docs/Technical%20Documents/InterFuse%20S%20Surgical%20Technique%20-%20International%20Version.pdf, accessed on Sep. 20, 2014, pp. 1-17.

"INTERSPINOUS," accessed at https://web.archive.org/web/20131123025814/http://www.thespinemarketgroup.com/p/interspinous-devices.html, accessed on Sep. 20, 2014, pp. 1-12.

"Prodisc-C Nova. Cervical disc prosthesis to restore disc height and maintain segmental motion," Technique Guide, 036.000.568—Synthes, accessed at http://www.synthes.com/MediaBin/International%20DATA/036.000.568.pdf, accessed on Sep. 20, 2014, pp. 1-30.

"X-spine announces FDA clearance of zygafix™ Facet Fusion System," accessed at https://web.archive.org/web/20131214104309/http://x-spine.com/x-spine-announces-fda-clearance-of-zygafix-facet-fusion-system/, May 8, 2013, p. 1.

Barad, J., "Lanx Adds New Device to Their Aspen Line for L5-S1 Fusion," accessed at https://web.archive.org/web/20121219073833/http://www.medgadget.com/2011/09/lanx-adds-new-device-to-their-aspen-line-for-I5-s1-fusion.html, Sep. 30, 2011, pp. 1-3.

Braun, B., "Posterior Thoracolumbar Stabilization System Surgical Technique," Aesculap S4® Spinal System, pp. 1-44.

Eglin, D., and Alini, M., "Degradable Polymeric Materials for Osteosynthesis: Tutorial," European Cells and Materials, vol. 16, pp. 80-91 (Dec. 19, 2008).

Eisner, W., "Lanx's aspen system achieves 94% fusion rate," accessed at http://ryortho.com/breaking/lanx039s-aspen-system-achieves-94-fusion-rate/, Sep. 19, 2012, pp. 1-2.

International Search Report and Written Opinion for International Application No. PCT/IB2014/000773, mailed on Sep. 8, 2014.

International Search Report and Written Opinion for International Application No. PCT/US2013/000984, mailed on Oct. 24, 2013.

Kettler, A., et al., "Are the spines of calf, pig and sheep suitable models for pre-clinical implant tests?" Eur Spine J., vol. 16, No. 12, pp. 2186-2192 (Dec. 2007).

Li, H. et al., "Effects of Pore Morphology and Bone Ingrowth on Mechanical Properties of Microporous Titanium as an Orthopaedic Implant Material," Materials Transactions, vol. 45, No. 4, pp. 1124-1131 (2004).

Mano, J. F., et al. "Bioinert, biodegradable and injectable polymeric matrix composites for hard tissue replacement: state of the art and recent developments," Composites Science and Technology, vol. 64, Issue 6, pp. 789-817 (2004).

Panjabi, M. M., et al., "Human Lumbar Vertebrae Quantitative Three-Dimensional Anatomy," Spine, vol. 17, No. 3, pp. 299-306 (Mar. 1992).

Smit, T. H., "The use of a quadruped as an in vivo model for the study of the spine—biomechanical considerations," Eur Spine J, vol. 11, No. 2, pp. 137-144 (Apr. 2002).

Wilke, H.-J., et al., "Biomechanical Comparison of Calf and Human Spines," Journal of Orthopedic Research, vol. 14, No. 3, pp. 500-503 (May 1996).

"Clspinedisc," accessed at http://www.ackermannmedical.com/#!cspine-disc-en/cII3c, accessed on Feb. 3, 2015, pp. 2.

"Precision Spine & Pain Clinic: Overview of Spinal Anatomy," accessed at http://web.archive.org/web/20130126154705/http://www.precisionspine.com.au/html/conditions_overview.html, accessed on Apr. 14, 2016, pp. 3.

"Spinal Conditions Treated," accessed at http://www.precisionhealth.com.au/services/pain-management/conditions-treated/spinal-conditions, accessed on Apr. 14, 2016, pp. 1-4.

"The coflex® Interlaminar Implant and the the coflex-F® Interlaminar Stabilization System," accessed at https://web.archive.org/web/20130624072256/http://spinerevolution.com/coflex/, accessed on Feb. 3, 2015, pp. 3.

Davis, W., et al., "Modern spinal instrumentation. Part 1: Normal spinal implants," Clinical Radiology, vol. 68, No. 1, pp. 64-74 (Jan. 2013).

(56) References Cited

OTHER PUBLICATIONS

Moreland, D.B., et al., "Anterior cervical discectomy and fusion with implantable titanium cage: initial impressions, patient outcomes and comparison to fusion with allograft," The Spine Journal, vol. 4, No. 2, pp. 184-191 (Mar.-Apr. 2004).

\* cited by examiner

SIDE VIEW

FRONT VIEW

SPINE STABILIZATION DEVICE

CROSS-REFERENCE TO RELATED APPLICATIONS

This Application is the U.S. National Stage filing under 35 U.S.C. §371 of PCT Application Ser. No. PCT/IB2014/000773 filed on Feb. 28, 2014, which claims priority under 35 U.S.C. §119(a) and 35 U.S.C. §365(b) to PCT Application Ser. No. PCT/AU13/000984 filed on Aug. 30, 2013. The disclosures of the PCT Applications are hereby incorporated by reference in their entireties.

BACKGROUND

Unless otherwise indicated herein, the materials described in this section are not prior art to the claims in this application and are not admitted to be prior art by inclusion in this section.

Surgical techniques are often used to treat spinal disorders. Spinal fusion is one such technique that may be indicated in circumstances where the spine is incapable of correctly performing key functions or where a patient experiences significant discomfort and pain due to deterioration, misalignment, and impingement on related nerves. Spinal fusion often involves use of artificial implants that are surgically positioned to bridge between and stabilize adjacent vertebrae. The stabilization implants may promote fusion via bone formation between the adjacent vertebrae. Such implants often involve the use of screws or other similar fasteners to ensure ongoing stability and provide a stable mechanical environment to allow bone formation as to provide sufficient mechanical properties to stabilize the spine.

SUMMARY

The following summary is illustrative only and is not intended to be in any way limiting. In addition to the illustrative aspects, embodiments, and features described above, further aspects, embodiments, and features will become apparent by reference to the drawings and the following detailed description.

The present disclosure generally describes a spinal stabilization device to facilitate spinal fusion. The spinal stabilization device may include an inter-transverse process implant including a first end including a first curved portion adapted to be in contact with a portion of a first vertebra of an adjacent vertebral pair, a second end including a second curved portion adapted to be in contact with a portion of a second vertebra adjacent to the first vertebra, and a middle portion extending between the first end and the second end, at least a portion of the middle portion adapted to be positioned between the first vertebra and the second vertebra.

The present disclosure also describes a spinal stabilization device to facilitate spinal fusion, including a first end adapted to be in contact with a first vertebra of an adjacent vertebral pair, a second end adapted to be in contact with a second vertebra of the adjacent vertebral pair, and a middle portion extending between the first end and the second end, at least a portion of the middle portion adapted to be positioned between the first vertebra and the second vertebra. The first vertebra may be a relatively superior vertebra and the second vertebra may be a relatively inferior vertebra of the adjacent vertebral pair.

The present disclosure also describes a spinal stabilization device to facilitate spinal fusion, including a plate fixation device configured to extend between a first pedicle screw inserted within a first vertebra and a second pedicle screw inserted within a second vertebra, where the plate fixation device includes one or more holes configured to accommodate insertion of the first and/or the second pedicle screws. The plate fixation device may include a locking mechanism to accommodate coupling with the first and/or the second pedicle screw such that when the first and/or the second pedicle screw may be inserted within the one or more holes, the plate fixation device may be compressed against the first vertebra and the second vertebra.

The present disclosure further describes a method to achieve spinal fusion, including inserting a spinal stabilization device between an adjacent vertebral pair such that a first end of the spinal stabilization device may be in contact with a first vertebra of the adjacent vertebral pair, and a bifurcated second end of the spinal stabilization device may be in contact with a second vertebra of the adjacent vertebral pair such that the bifurcated second end straddles a portion of the second vertebra.

The present disclosure also describes a method to achieve spinal fusion, including inserting an elongated plate between an adjacent vertebral pair, such that a first end of the plate may be in contact with a posterior lamina of a first vertebra of the adjacent vertebral pair, and a second end of the plate may be in contact with a posterior lamina of the second vertebra, and where a middle portion of the plate extending between the first end and the second end may be adapted to be positioned between the first vertebra and the second vertebra.

The present disclosure further describes a method to achieve spinal fusion, the method including inserting an inter-transverse process implant between a first vertebra and a second vertebra of an adjacent vertebral pair such that a first end of the implant may be in contact with a first transverse process of the first vertebra of the adjacent vertebral pair, a second end of the implant may be in contact with a second transverse process of the second vertebra of the adjacent vertebral pair, and a middle portion configured in a substantially curved shape extends between the first end and the second end in one of a posterior or an anterior configuration with respect to the adjacent vertebral pair.

The present disclosure further describes a method to achieve spinal fusion, including inserting an inter-transverse process implant between a first vertebra and a second vertebra of an adjacent vertebral pair such that a first end including a first curved portion may be in contact with a portion of a first vertebra of an adjacent vertebral pair, a second end including a second curved portion may be in contact with a portion of a second vertebra adjacent to the first vertebra, and a middle portion coupling the first end and the second end extends between the first vertebra and the second vertebra.

The present disclosure also describes a method to increase stability of an adjacent vertebral pair of a spine. The method may include selecting a spinal stabilization device having dimensions and mechanical parameters to achieve the increase in stability between the adjacent vertebral pair, preparing a portion of a surface of a first vertebra and a second vertebra of the adjacent vertebral pair employing a vibrational technique to receive the spinal stabilization device, and implanting the spinal stabilization device at a location relative to the adjacent vertebral pair.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
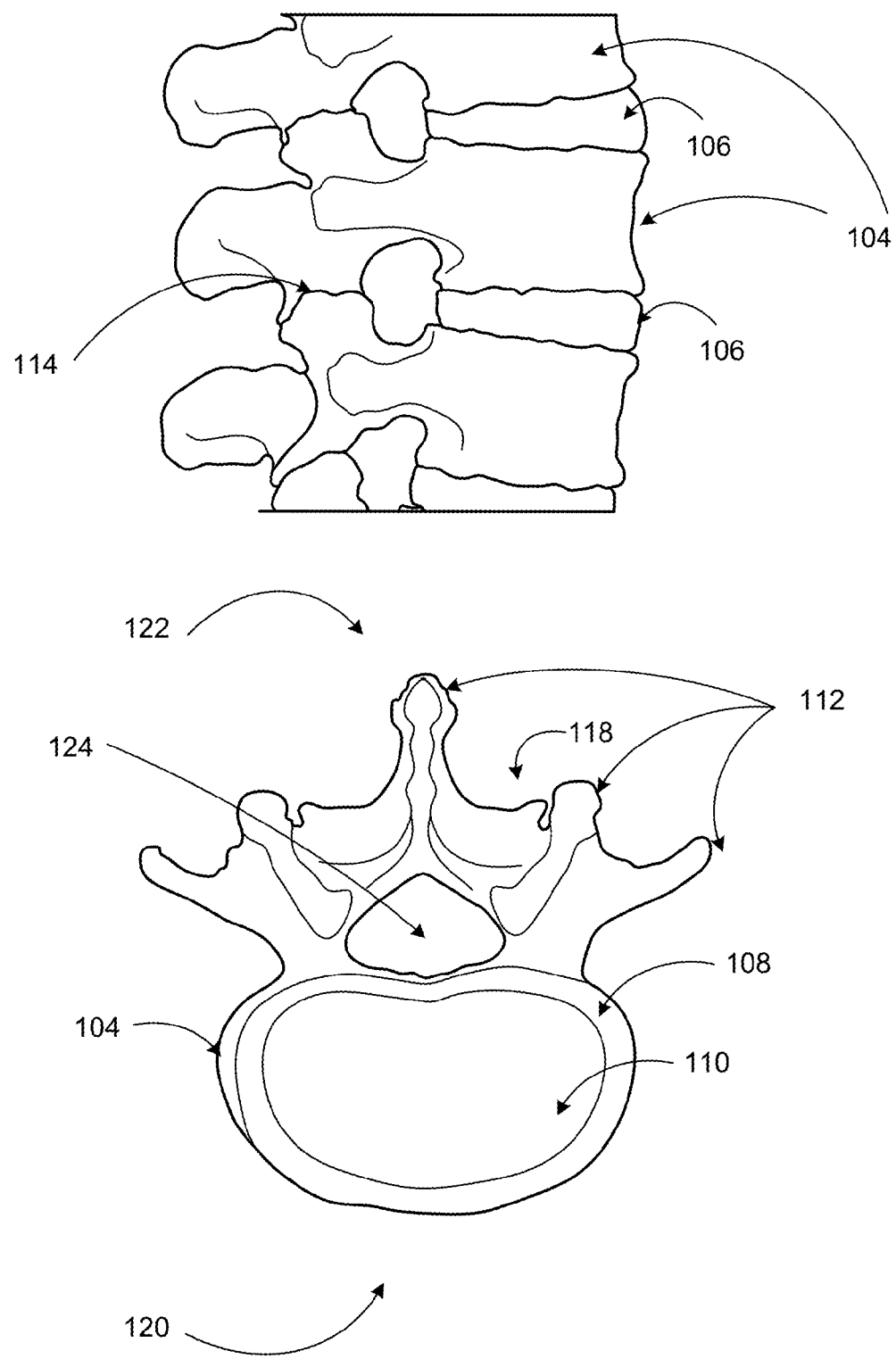
FIG. 1 illustrates an anatomy of an example spinal column and cross section of a vertebra.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. The aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to compositions, methods, apparatus, systems, and/or devices related to providing a spine stabilization device.

Briefly stated, technologies are generally provided for devices, systems, and methods to provide spinal fixation, spinal stabilization, and/or spinal fusion. An example device may include a first end and a second end with a middle portion extending between the first and second end. The first end may be configured to be in contact with a portion of a first or upper vertebra and the second end may be configured to be in contact with a portion of a second or lower vertebra in an adjacent vertebral pair. Portions of the vertebra which may be in contact with the device may include lamina, processes, vertebral bodies, and facet joints. The example devices may include bone engagement features, such as screws or similar fasteners, to enhance stabilization and fixation when in contact with the vertebrae. Additionally, the devices may include a bone integration feature to promote bone growth and to facilitate fusion between the vertebrae.

In some figures and associated descriptions below, some portions of anatomy have been intentionally omitted and/or represented in varying proportions in order to facilitate viewing and description of the described spinal stabilization devices, according to embodiments herein.

FIG. 1 illustrates an anatomy of an example spinal column and cross section of a vertebra, arranged in accordance with at least some embodiments as described herein.

An example human spinal column includes 33 vertebrae, including 24 articulating vertebrae in upper regions of the spine (i.e. cervical, thoracic, and lumbar regions), and nine fused vertebrae in a lower region below the lumbar region forming a sacrum and a coccyx of the spine. The vertebrae are separated by intervertebral discs 106 that provide separation and cushioning between the vertebrae. The vertebrae provide for muscle connection to enable movement of the spine, and to allow the spine to support the weight of the upper body. The spinal column also provides protection for the spinal cord.

An example vertebra includes an anterior portion 120, or a vertebral body 104, and a posterior portion 122, which includes lamina 118, pedicles, processes 112 (including transverse processes, a spinous process, and superior and inferior articular processes), and facet joints 114. The anterior portion 120 and posterior portion 122 together enclose a foramen 124 that forms a canal for protection of the spinal cord. The vertebral body 104 is composed of hard cortical bone on the outside which forms a rim 108 around a circumference of the vertebral body 104, and less dense, or spongy, cancellous bone 110 on the inside. The intervertebral discs 106 are sandwiched between adjacent vertebral bodies and are attached to the rims 108 of each vertebral body 104 via a bony endplate. The intervertebral discs 106 are soft, compressible discs that separate the vertebral bodies 104, acting as shock absorbers for the spine, and allowing the spine to flex, bend, and twist. Over time, the intervertebral discs 106 can break down, or degenerate, putting pressure on the spinal cord and nerves, which can lead to pain and can affect nerve function.

A spinal fusion is a procedure designed to alleviate symptoms of disc degeneration and other disc issues, including herniation, spondylolisthesis, kyphosis, and lordosis, for example. The spinal fusion may involve bone formation between two or more adjacent vertebrae to cause the two or more adjacent vertebrae to permanently fuse together in order to eliminate motion in the fused segment of the spine, and thereby decrease and/or eliminate the back pain created by the motion of the spine. Some existing methods to achieve spinal fusion may include implants placed between adjacent vertebrae to provide fixation and stabilization. In some existing techniques, bone graft material may be inserted between the vertebrae to promote bone growth through the implants, and plates, screws, or rods or other fixation devices may be employed to hold the vertebrae together while the bone graft fuses the vertebrae together.

A system according to embodiments may provide low-profile spinal stabilization devices to enable fixation and stabilization between adjacent vertebrae, and to facilitate eventual fusion between the adjacent vertebrae. Example stabilization devices, according to embodiments, may be configured to be in contact with portions of upper and lower vertebrae of an adjacent vertebral pair to stabilize the vertebrae while the vertebrae fuse together.

Figure 2:
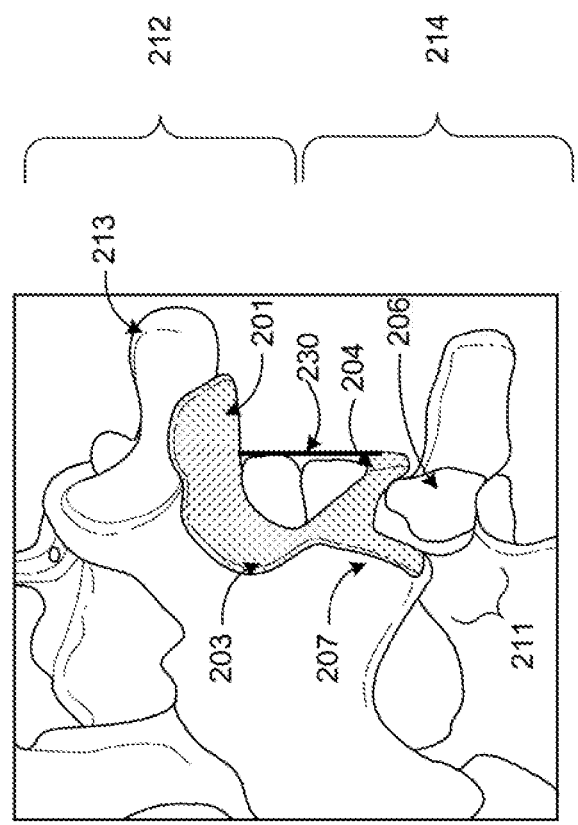
FIG. 2 illustrates an example spinal stabilization device integrated within a facet joint between adjacent vertebrae.
Figure 2:
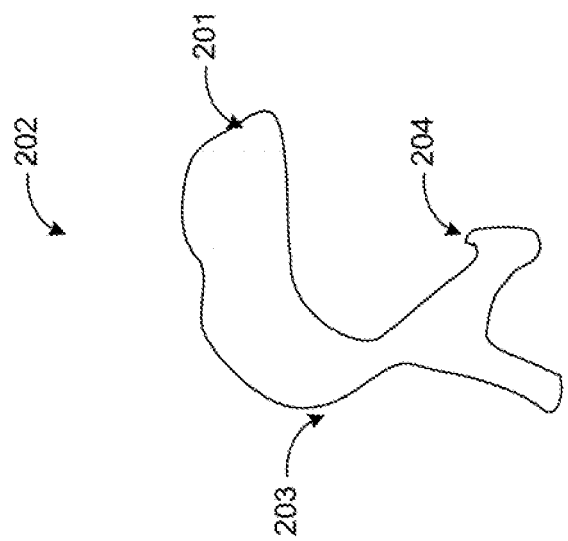

FIG. 2 illustrates an example spinal stabilization device 202 integrated within a facet joint between adjacent vertebrae, arranged in accordance with at least some embodiments as described herein.

In a system according to embodiments, a spinal stabilization device 202 or implant may be employed to minimize and/or prohibit motion between adjacent facets, or within a facet joint 211, of an upper and lower vertebra. The facet joint, or the Zygapophyseal or Apophyseal joint, is a joint between a superior articular process 206 of a lower vertebra 214 and an inferior articular process 207 of an adjacent upper vertebra 212. There are two facet joints in each vertebral pair, one on a posterior right side and another on a posterior left side of the vertebra.

An example spinal stabilization device or implant to prohibit motion between adjacent facets may be a spinal stabilization device 202 having a first end 201 and a second end 204 with a middle portion 203 extending between the first end 201 and the second end 204. A stabilizing cross member 230 may extend from the first end 201 to the second end 204. In an example embodiment, one or both ends of the spinal stabilization device 202 may be bifurcated into a "y-shaped" end (i.e. a bifurcated end). For example, the second end 204 may be bifurcated into a forked or "y-shaped" end such that that the spinal stabilization device 202 may substantially resemble a lambda shape when viewing the device from a front view. The bifurcated second end 204 may be configured to be seated upon a superior articular process 206 of a facet joint of a lower vertebra 214 of an adjacent vertebral pair. When seated upon the superior articular process 206, the bifurcated second end 204 may straddle the superior articular process 206 of the facet joint such that a prong of the bifurcated second end 204 may be positioned intra-facet of the adjacent vertebra pair to anchor the spinal stabilization device 202 in position. Seating the bifurcated second end. 204 upon the superior articular process 206 of the facet joint may enable the spinal stabilization device 202 to experience minimal movement and a reduced instance of migration once in position.

In a system according to embodiments, the first end 201 of the spinal stabilization device 202 may be configured to be in contact with a portion of an upper vertebra 212 of the adjacent vertebral pair. For example, the first end 201 of the spinal stabilization device 202 may be arranged to be in contact with an underside of a superior articular process, an inferior surface of a pedicle, or an inferior surface of a transverse process 213 of the upper vertebra 212. In some embodiments, the first end 201 and/or the second end 204 may be contoured such that a channel of the first end 201 may be formed to receive the portion of the upper vertebra 212. The spinal stabilization device 202 may be implanted extraosseously such that the first end 201 rests upon the upper vertebra 212 and the second end 204 rests upon the lower vertebra 214 without active fixation.

Additionally, in other embodiments, one or both of the first end 201 and the second end 204 may be anchored to the portion of the upper vertebra 212 and the lower vertebra 214 employing a mechanical fixation mechanism to stabilize the spinal stabilization device 202 in position and to prevent undesired movement and migration of the spinal stabilization device 202 once in position. Example fixation mechanism may include screws, clamps, sutures, hooks, wires, roughened surfaces, and other similar fixation mechanism. Furthermore, the first end 201 and the second end 204 may also include a bone engagement feature to prevent migration. The bone engagement feature may be adapted to aggravate, pierce or scratch a bone, such as the vertebrae, and/or its related periosteum, to trigger an osteogenic, or a bone healing, response in the bone surface. An example bone engagement feature may include hooks, spikes, and a modified or textured surface to enable the first and/or second ends to engage with the vertebra to prevent movement and migration, at least temporarily. The surface may be modified or textured with etching, pores or other features to provide a roughened surface for bone growth to engage the stabilization device 202. In some scenarios, a surface of one or more of the upper vertebra and the lower vertebra may be prepared to receive the spinal stabilization device 202 prior to insertion of the spinal stabilization device 202 by decorticating the surface prior to insertion of the spinal stabilization device 202. In other embodiments, the spinal stabilization device 202 may be configured to be passively maintained in position between the adjacent vertebra in response to pressure from surrounding ligaments, musculature, and tissue without an active fixation mechanism.

In another example embodiment, a combination of mechanical and chemical fixation mechanisms may be employed together to stabilize the spinal stabilization device 202 in position and to prevent undesired movement and migration of the spinal stabilization device 202 once in position. For example, a mechanical mechanism, such as screws, wires, hooks, and other similar mechanisms, may be combined with a chemical fixation mechanism such as a biological fixation, compound, and/or glue. Some chemical fixation mechanisms may include creating an irritation on a bone surface (e.g., through etching, scratching, and/or texturizing) to facilitate bone growth, and coating the surface with a material to aid in bone growth. Some example coating materials may include a hydroxyapatite coating, calcium phosphate coatings, Arginylglycylaspartic acid (RGD) sequences, and other peptides configured to facilitate bonding and bone growth.

In an example embodiment, the middle portion 203 between the first end 201 and the second end 204 may be curved from the first end 201 to the second end 204 to substantially follow a natural bony anatomy between the upper vertebra 212 and the lower vertebra 214. The curved middle portion 203 may be positioned in situ such that the middle portion 203 extends between the first end 201 and the second end 204 across vertebrae of the adjacent vertebral pair, or alternatively, the middle portion 203 may extend across lamina of the adjacent vertebral pair.

In some embodiments, an expansion force may be provided between the first end 201 and the second end 204 along the middle portion 203 to facilitate holding the spinal stabilization device 202 in place between the upper vertebra 212 and lower vertebra 214 of the adjacent vertebra pair. The expansion force may also be configured to increase a space between facets as desired in order to compensate for detected spinal misalignments. In other embodiments, a compression force may be provided between the first end 201 and the second end 204 along the middle portion 203 to enable a space between facets to be reduced to also compensate for detected spinal misalignments. For example, two facet implants may be employed together to reduce a facet space on one side of a vertebra while increasing a facet space on the other side of the vertebra. Dimensions, such as a shape and size, of the spinal stabilization device 202 may be selected pre-operatively based on patient anatomy specifics, and desired results.

In an example embodiment, the spinal stabilization device 202 may be composed from a polymer, a metal, an alloy, or a combination thereof, which may be biocompatible. For example, the spinal stabilization device 202 can be formed from titanium or a titanium alloy. Other suitable metals may include stainless steel, cobalt-chromium alloys, and tantalum. Additionally, metal alloys having varying physical properties such as shape memory capability, such as nickel titanium or spring stainless steel alloys, may be used. In another embodiment, the spinal stabilization device 202 can be formed from a suitable polymer including non-degradable polymers, such as polyetheretherketone (PEEK) and polyethylene (PE), as well as modified versions of these materials (for example, PEEK+calcium phosphates and PE+vitamin E, metal coatings, or surface texturing). Additional non limiting polymers may include polymers, such as polyether-block co-polyamide polymers, copolyester elastomers, thermoset polymers, polyolefins (e.g., polypropylene or polyethylene, including high density polyethylene (HDPEs), low-density polyethylene (LDPEs), and ultrahigh molecular weight polyethylene (UHMWPE)), polytetrafluoroethylene, ethylene vinyl acetate, polyamides, polyimides, polyurethanes, polyvinyl chloride (PVC), fluoropolymers (e.g., fluorinated ethylene propylene, perfluoroalkoxy (PFA) polymer, polyvinylidenefluoride, etc.), polyetheretherketones (PEEKs), PEEK-carbon fiber composites, Polyetherketoneketones (PEKKs), poly(methylmethacrylate) (PMMA), polysulfone (PSU), epoxy resins and silicones. Additionally starch based polymers may be used.

Additional materials may include carbon and polyaramid structures, glass or fiberglass derivatives, ceramic materials, and artificial biocompatible protein derivatives (recombinant derived collagen). In other embodiments, the stabilization device 202 may be made of a metal and/or alloy backbone with a polymer shell, or a sandwich style composition of any number of layers of any of the materials listed herein. Various layers may be bonded to each other to provide for single layer composition of metal(s), alloys, and/or polymers. In another embodiment, a polymer backbone may be used with a metal and/or metal alloy shell.

Additionally, at least a portion of the spinal stabilization device 202 may include a bone integration surface to promote bone ingrowth, on-growth, and/or through-growth between the upper vertebra 212, the lower vertebra 214, and the spinal stabilization device 202 to facilitate fusion between the upper vertebra and the lower vertebra and/or to facilitate fusion between the spinal stabilization device 202 and one or both of the upper and lower vertebrae. The bone integration surfaces can comprise a three-dimensional space to allow bone integration into and/or onto portions of the spinal stabilization device 202. The three dimensional space can be provided by a three-dimensional substrate, for example beads, and/or by the provision of holes through the bone integration portions. Other methods for achieving bone integration can include the provision of an appropriate surface topography, for example a roughened or textured area and/or by the provision of osteoconductive coatings, such as calcium phosphates. The bone integration surface may enable the spinal stabilization device 202 to provide a metal and/or polymeric scaffold for tissue integration to be achieved through the spinal stabilization device 202. In various embodiments, various materials may be used to facilitate, stimulate or activate bone growth. A non-limiting list of materials may include hydroxyapatite (HA) coatings, synthetic bioabsorbable polymers such as poly (α-hydroxy esters), poly (L-lactic acid) (PLLA), poly(glycolic acid) (PGA) or their copolymers, poly(DL-lactic-co-glycolic acid) (PLGA), and poly(ε-caprolactone) (PLC), poly(L-lactide) (LPLA), (DLPLA), poly(e-caprolactone) (PCL), poly(dioxanone) (PDO), poly(glycolide-co-trimethylene carbonate) (PGA-TMC), poly(lactide-co-glycolide), polyorthoesters, poly (anhydrides), polyhydroxybutyrate, poly(l-lactide-co-glycolide) (PGA-LPLA), cyanoacrylates, poly (dl-lactide-co-glycolide) (PGA-DLPLA), poly(ethylene carbonate), poly(iminocarbonates), poly(l-lactide-co-dl-lactide) (LPLA-DLPLA), and poly(glycolide-co-trimethylene carbonate-co-dioxanone) (PDO-PGA-TMC).

Furthermore, at least a portion of the spinal stabilization device 202 may be treated or coated with a calcium material, such as calcium deposits, calcium phosphate coatings, calcium sulfates, modified calcium salts such as Magnesium, Strontium and/or Silicon substituted calcium phosphates, RGD sequences, collagen, and combinations thereof in order to enhance a strength of bone ingrowth, on-growth, and/or through-growth between the vertebrae and with the spinal stabilization device 202. The calcium deposits and/or coatings may enable newly forming bone to draw from the calcium deposits when forming, and to not deplete naturally occurring calcium from bones of the spinal column which may result in a weakening of the spinal column.

Example techniques for insertion and implantation of the spinal stabilization device 202 may include an open surgical procedure and/or a minimally invasive surgical procedure, where lateral and posterior approaches may enable convenient access to the facet joint(s) 211. An example procedure may include dissection and exposure to access a targeted facet joint, removal of at least a portion of facet joint cartilage, and optional decortication of the receiving vertebral bone areas. Additionally, a portion of the facets of the facet joint(s) 211 may be trimmed and shaped employing specialized tools such as rasps to prepare the facet to receive the implant. Subsequently, one end of the spinal stabilization device 202 may be inserted into the facet joint 211 and the other end may be attached to a portion of the upper vertebra 212 as described above. Specialized tools, such as guide wires, cannulated drills, tubular retractors, and the like under fluoroscopy monitoring may also be employed to facilitate implantation. In an example minimally invasive procedure, minimal bone preparation and minimal exposure of bony elements of the spine may be required in order to insert the device. Implantation of the device may be achieved employing ultrasound or radiographic guided implantation, where the device may include a plurality of radiographic markers to enable the surgeon to radiographically monitor a position of the device and to insert the device into position employing the radiographic imaging.

In a system according to embodiments, the spinal stabilization device may be customized for individuals based on a predetermined anatomy of each individual. For example, a detailed anatomical scan may be performed of an individual's vertebral anatomy employing, for example, a computed tomography (CT) scan, an ultrasound and/or a magnetic resonance imaging (MRI) scan. Based on the detailed vertebral scan, an individual-specific spinal stabilization device may be created to match the individual's anatomy. For example, bone contacting portions of the device, such as a bone contacting channel or a groove, may match a surface of the bone. Additionally, dimensions of the device may match a space between vertebrae where the device may be implanted. In some examples, after a scan has been performed, a surgeon or physician may also apply customizations to correct for deformities and/or to induce desired effects of the implant. The scans may also enable the physician to predict a range of stresses on the vertebrae, to monitor for nerve impingements, and to evaluate potential ranges of motion for a manufactured implant. Based on the scan and physician specifications, the spinal stabilization device may be manufactured employing three-dimensional printing techniques, or other manufacturing techniques. The spinal stabilization device may also be constructed from a malleable material to enable manipulation in situ by the physician to position the device into a desired position.

Figure 3A:
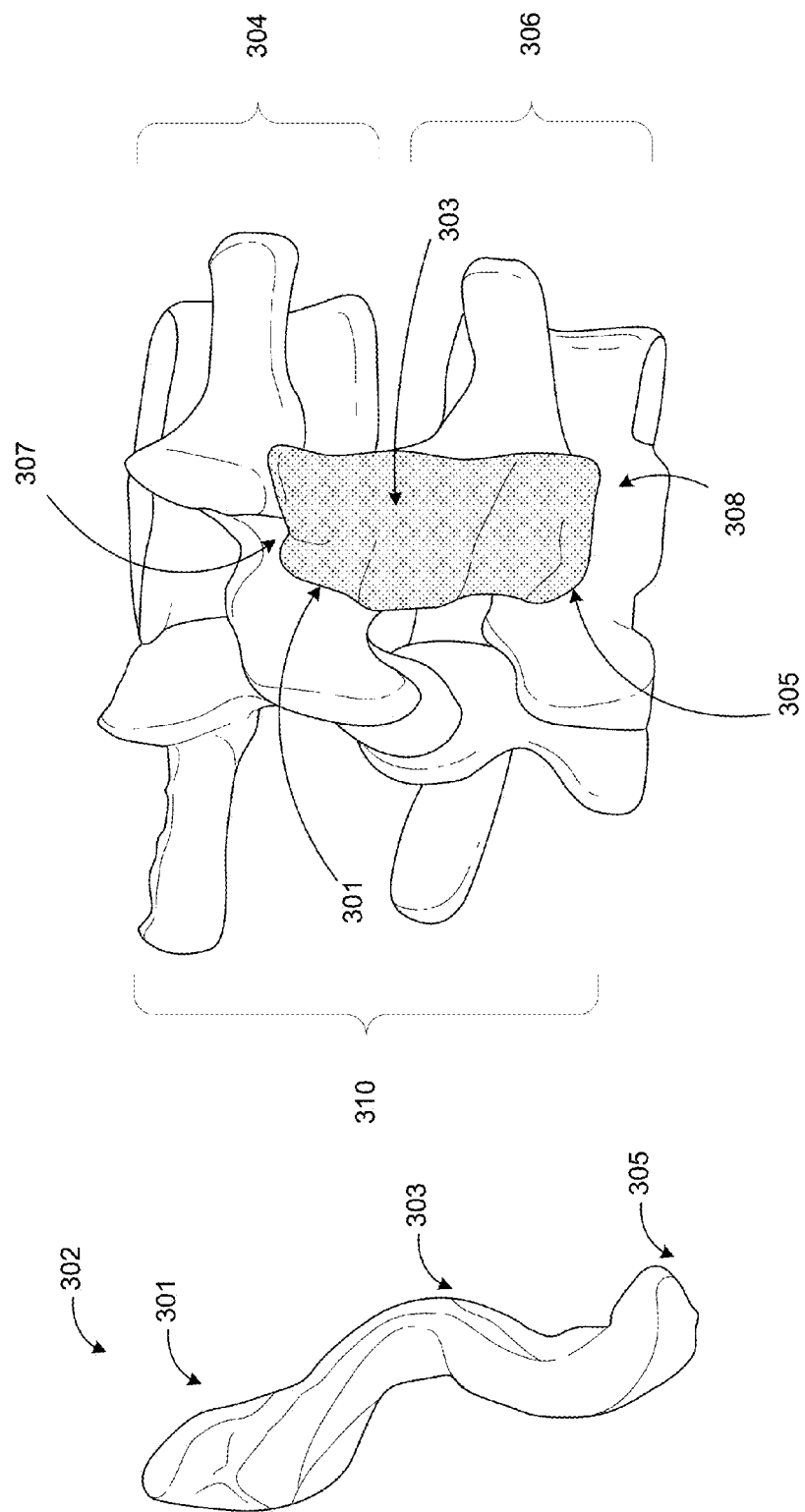
FIGS. 3A-3C illustrate example configurations of a spinal stabilization device connecting lamina of adjacent vertebrae.
Figure 3B:
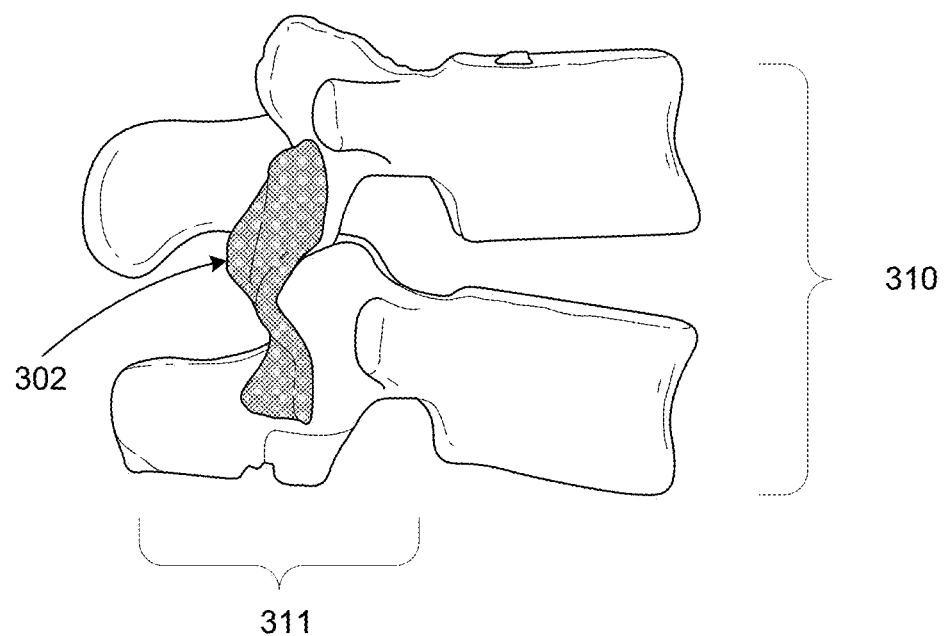
Figure 3C:
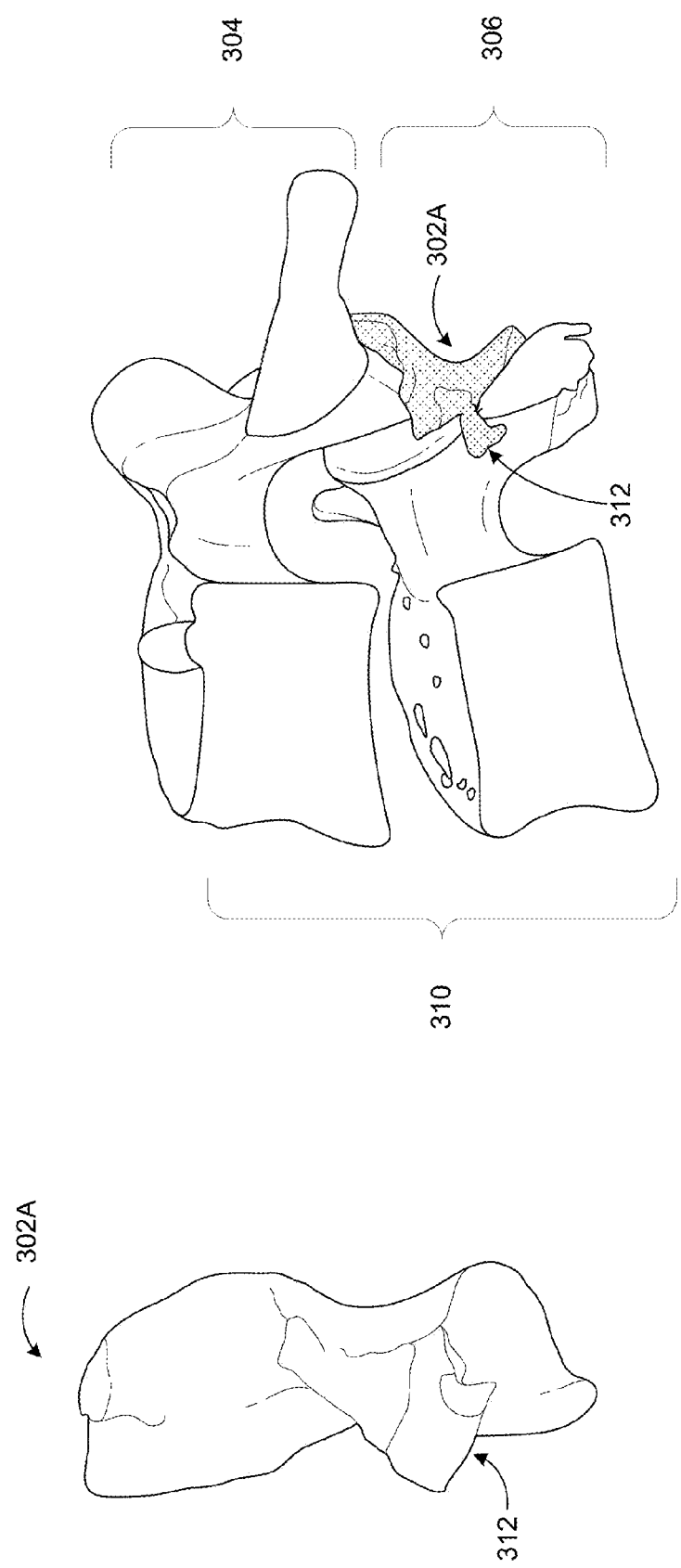

FIGS. 3A-3C illustrate example configurations of a spinal stabilization device connecting lamina of adjacent vertebrae, arranged in accordance with at least some embodiments as described herein.

In a system according to embodiments, as illustrated in FIG. 3A, a spinal stabilization device or implant may be employed to prohibit motion between an upper vertebra 304 and a lower vertebra 306 of an adjacent vertebral pair 310 through engagement with lamina 307, 308 of the upper vertebra 304 and the lower vertebra 306. The spinal stabilization device may be a laminar plate 302 configured to engage with a posterior surface of lamina (e.g., an upper lamina 307 and a lower lamina 308) of an adjacent vertebral pair 310. The laminar plate 302 may be an elongated plate 302 configured to extend between a first vertebra (e.g. the upper vertebra 304) and a second vertebra (e.g. the lower vertebra 306) of an adjacent vertebral pair 310. A first end 301 of the plate 302 may be in contact with a posterior upper lamina 307 of the first or the upper vertebra 304, a second end 305 of the plate 302 may be in contact with a posterior lower lamina 308 of the second or the lower vertebra 306, and a middle portion 303 of the plate 302 may extend between the first end 301 and the second end 305 to connect and stabilize the upper vertebra and the lower vertebra. The middle portion 303 of the plate 302 may be contoured to substantially follow a natural bony anatomy of a posterior portion 311 of the adjacent vertebral pair 310, as illustrated FIG. 3B demonstrating a side view of the plate 302.

In a further embodiment, as illustrated in FIG. 3C, a laminar plate 302A may include a locking component 312 configured to extend from the plate 302A into a facet joint between the first or the upper vertebra 304 and the second or the lower vertebra 306. The locking component 312 may be a hook configured to insert within the facet joint to stabilize the plate 302A in position between the first vertebra and the second vertebra. The locking component 312 may facilitate a fusion of the facet joint.

In a system according to embodiments, one or both of the first end 301 and the second end 305 of the plate 302 may be anchored to the lamina 308 of the upper vertebra 304 and the lower vertebra 306 employing a mechanical fixation mechanism to stabilize the device in position and to prevent undesired movement and migration of the device once in position. Example fixation mechanisms may include screws, clamps, sutures, hooks, wires, roughened surfaces, and other similar fixation mechanisms, as described above. Additionally, the first and second ends may also include a bone engagement feature, as also described above, to prevent migration. Example bone engagement features may include hooks, spikes, and a modified or textured surface to enable the first and/or second ends to engage with the vertebra to prevent movement and migration. The bone engagement feature may also trigger an osteogenic response. In some scenarios, a surface of one or more of the first vertebra and the second vertebra may be prepared to receive the spinal stabilization device prior to insertion of the spinal stabilization device by decorticating the surface prior to insertion of the spinal stabilization device. In other embodiments, the device may be configured to be passively stabilized between the adjacent vertebra in response to pressure from surrounding ligaments, musculature and tissue without an active fixation mechanism.

The laminar plate (e.g. 302 and 302A) may be composed from a polymer, a metal, an alloy, or a combination thereof. Example materials may be as described herein.

Additionally, at least a portion of the plate 302 may include a bone integration surface to promote bone ingrowth, on-growth, and/or through-growth between the first vertebra, the second vertebra, and the plate 302 to facilitate fusion between the first vertebra and the second vertebra and/or to facilitate fusion between the plate 302 and one or both of the first and second vertebrae. As discussed above, the bone integration surface can include an appropriate surface topography, for example a roughened or textured area, and/or osteoconductive coatings, such as calcium phosphates, on the surface to enable the plate 302 to provide a metal and/or polymeric scaffold for tissue integration to be achieved through the plate 302.

Furthermore, at least a portion of the plate 302 may be treated or coated with a calcium material, such as calcium deposits and coatings as described herein to enhance a strength of bone ingrowth, on-growth, and/or through-growth between the vertebrae and with the plate 302. The coated calcium deposits may enable newly forming bone to draw from the calcium deposits when forming, and to not deplete naturally occurring calcium from bones of the spinal column which may result in a weakening of the spinal column.

Example techniques for insertion and implantation of the plate 302 may include an open surgical procedure and/or a minimally invasive surgical procedure, where lateral and posterior approaches may enable convenient access to the posterior lamina (e.g., 307 and 308). An example procedure may include dissection and exposure to access a targeted vertebral pair and optional decortication of the receiving vertebral bone areas, such as the lamina 307 and 308. Subsequently, one end of the plate 302 may be attached to an upper vertebra 304 and the other end may be attached to the lower vertebra 306 as described above. Specialized tools, such as guide wires, cannulated drills, tubular retractors, fluoroscopy monitoring, radiographic markers and imaging may also be employed to facilitate implantation through minimally invasive procedures.

FIGS. 4A-4D illustrate example configurations of an inter-transverse fusion device connecting transverse processes of adjacent vertebrae in an anterior configuration, arranged in accordance with at least some embodiments as described herein.

Figure 4A:
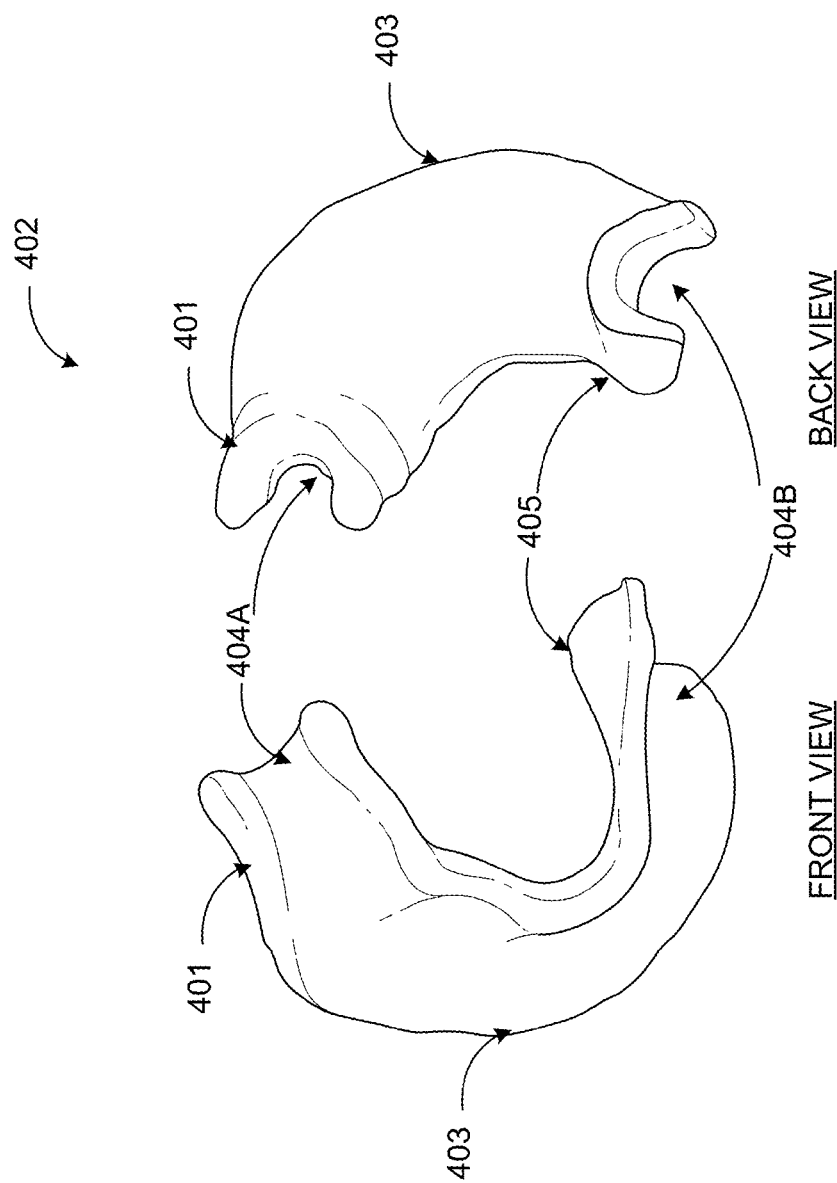
FIGS. 4A-4D illustrate example configurations of an inter-transverse fusion device connecting transverse processes of adjacent vertebrae in an anterior configuration.

As illustrated in FIG. 4A, a spinal stabilization device may include an inter-transverse process implant 402 configured to be inserted between transverse processes of a first vertebra and a second vertebra of an adjacent vertebral pair 410. A first end 401 of the implant 402 may be configured to be in contact with a first transverse process of the first, or upper, vertebra, and a second end 405 of the implant 402 may be configured to be in contact with a second transverse process of the second, or lower, vertebra. A middle portion 403 may extend between the first end 401 and the second end 405, and the middle portion 403 may be configured in a substantially curved shape to accommodate an anatomy of the spine between the transverse processes, and may include a channel (i.e. channel 404A and 404B) on a bone contacting side of the implant 402. The channel 404 may be contiguous from the first end 401 to the second end 405, where a first end of the channel is shown as 404A and the second end of the channel is shown as 404B in FIG. 4A.

In one example embodiment, the curved middle portion 403 may extend in an anterior configuration with respect to the adjacent vertebral pair 410, such that the curved middle portion 403 may follow an anterior aspect of a foramen along vertebral bodies of the adjacent vertebral pair 410. In another example embodiment, as will be discussed in further detail below in conjunction with FIGS. 5A-5B, the curved middle portion 403 may be in a posterior configuration with respect to the adjacent vertebral pair 410.

Figure 4B:
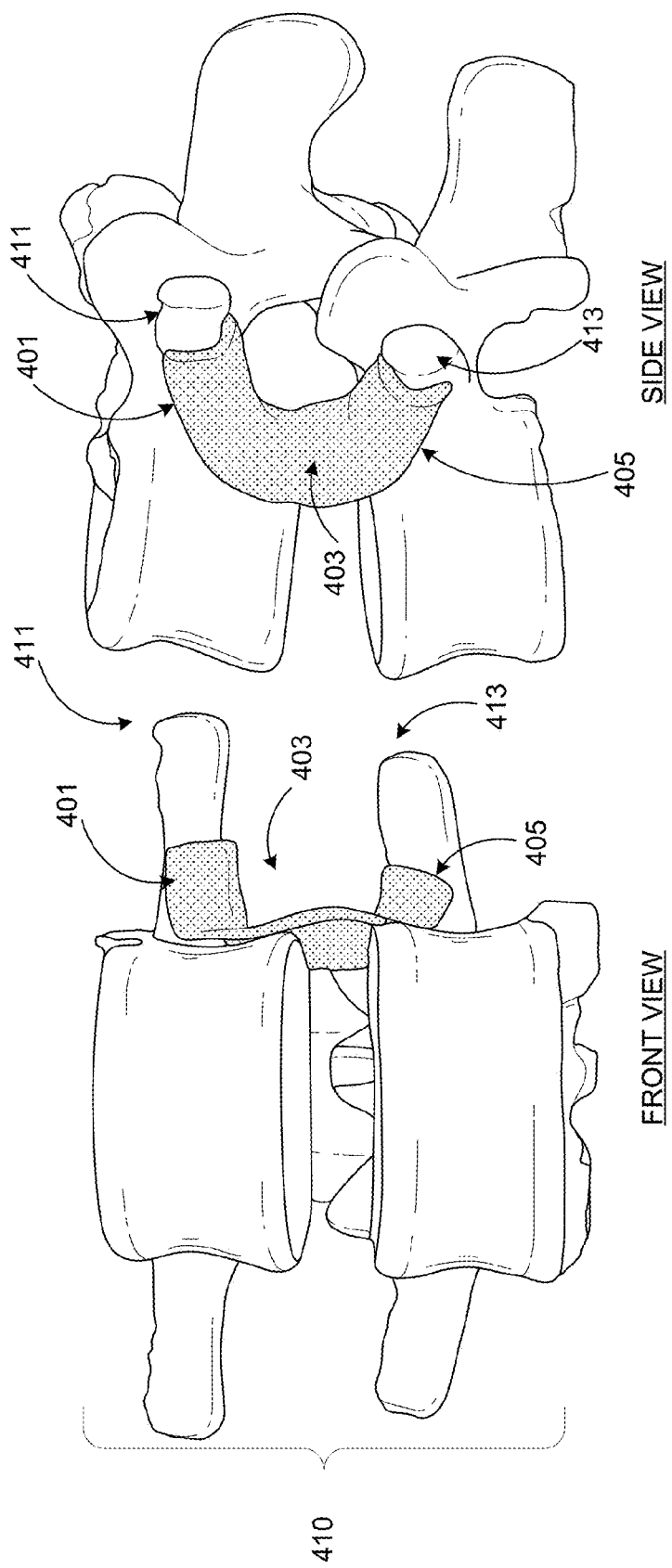

FIG. 4B illustrates a front view and a side view of the inter-transverse process implant 402 inserted in position between transverse processes (i.e. an upper transverse process 411 and a lower transverse process 413) of upper and lower vertebrae of the adjacent vertebral pair 410. A stabilizing cross member, such as the stabilizing cross member 230, may enhance a strength and a stability of the inter-transverse process implant 402 between the upper and lower vertebrae of the adjacent vertebral pair 410. In an example embodiment, the curved middle portion 403 may include a contoured channel 404, as described in FIG. 4A, or a groove along a bone contacting surface to substantially accommodate a natural bony anatomy of the anterior aspect of the foramen along the vertebral bodies and along the disc of the adjacent vertebral pair 410. In some examples, the bone contacting surface of the implant may be configured to be in contact with the bone such that about 10% to about 100% of the implant may be in contact and communicable with the bone. Additionally; when the bone contacting surface of the implant is in contact with a portion of the bone, there may be a slight offset of less than about 2 to about 300 micrometers to enable the bone to attach to the implant, however, in some scenarios, the implant may be offset further.

In an example embodiment, at least a portion of the bone contacting surface of the contoured channel 404 may include a bone integration surface to promote bone ingrowth, on-growth, and/or through-growth between the first vertebra, the second vertebra, and the implant 402 to facilitate fusion between the first vertebra and the second vertebra and/or to facilitate fusion between the device and one or both of the first and second vertebrae. The bone integration surface may include, for example, a roughened or textured area, or osteoconductive coatings, such as calcium phosphates. The bone integration surface may enable the device to provide a metal and/or polymeric scaffold for tissue integration to be achieved through the device. Additionally, at least a portion of the implant 402 may be treated or coated with a calcium material as described herein, to enhance a strength of bone ingrowth, on-growth, and/or through-growth between the vertebrae and with the implant 402. The bone integration surface may be present on one side of the implant 402 only, such as the bone contacting surface, so that there is no bony growth on the other side, which may prevent bone growth over nerves and other tissue.

Figure 4C:
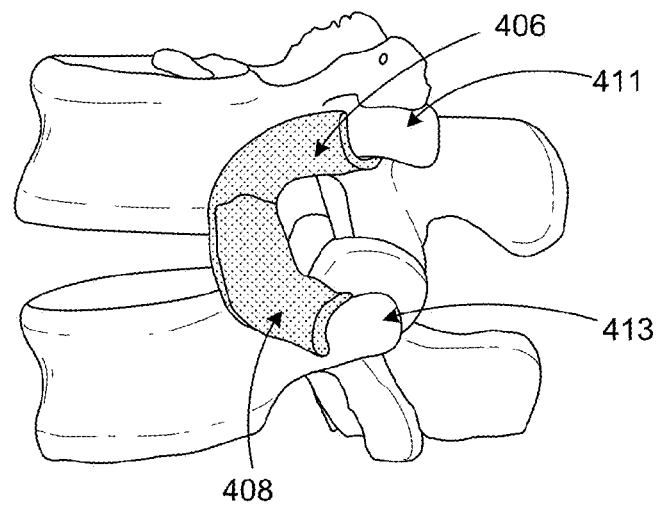
Figure 4C:
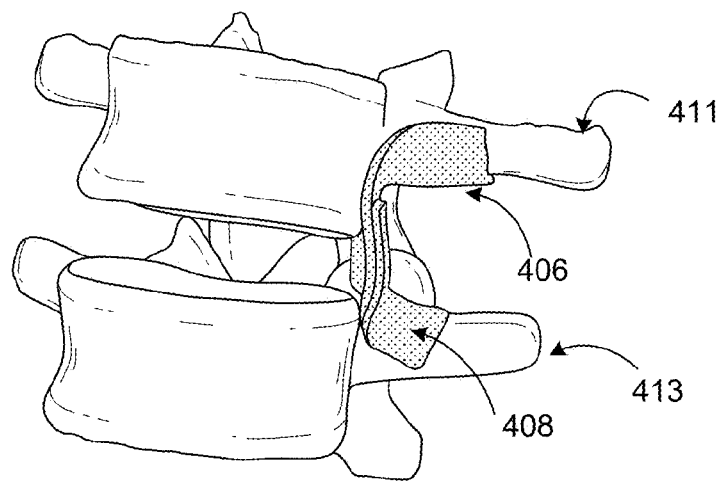

As illustrated in FIG. 4C, the inter-transverse process implant 402 may include at least two portions to facilitate implantation, including an upper portion 406 and a lower portion 408. The upper portion 406 and lower portion 408 may be inserted separately, and may be configured to be coupled together in situ. For example, the upper portion 406 may be attached to a portion of the upper transverse process 411, and the lower portion 408 may be attached to a portion of the lower transverse process 413. After insertion of both the upper and lower portions 408, the upper portion 406 and the lower portion 408 may be coupled together through a coupling mechanism, such as a snap fit, a Morse taper engagement, connecting tabs, by screwing the portions together, by gluing the portions together with a biocompatible glue, or other similar coupling mechanism.

Figure 4D:
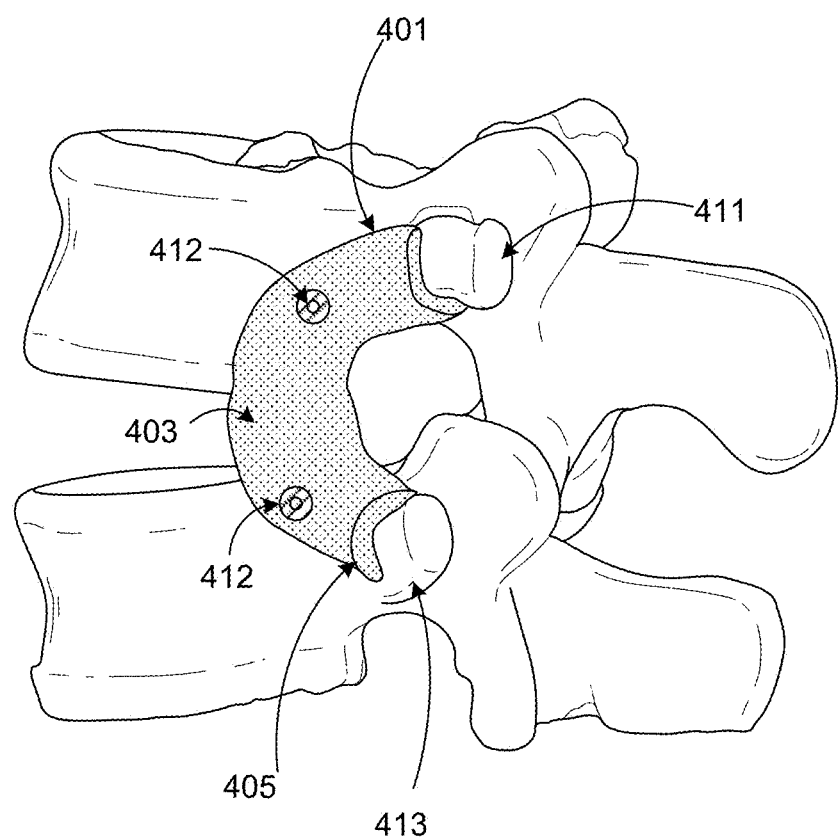

As illustrated in FIG. 4D, the inter-transverse process implant 402 may be anchored to the portion of the upper vertebra and the lower vertebra employing a mechanical fixation mechanism 412 to stabilize the device in position and to prevent undesired movement and migration of the implant once in position. Example fixation mechanisms 412 may include screws, clamps, sutures, hooks, wires, roughened surfaces, and other similar fixation mechanisms as previously described herein. The fixation mechanism 412 may be integrated with one or both of the first end 401 and the second end 405 of the implant 402, and may be configured to fix the first end 401 a portion of the upper vertebra, such as the upper transverse process 411 and the second end 405 to a portion of the lower vertebra, such as the lower transverse process 413.

In another embodiment, when the implant 402 includes upper and lower portions configured to be coupled together as described above, each of the upper and lower portions may be anchored to the upper transverse process 411 and the lower transverse process 413, respectively, employing fixation mechanisms 412. The first end 401 and the second end 405 of the implant 402 may also include a bone engagement feature to prevent migration and to trigger an osteogenic, or a bone healing, response in the bone surface. As previously discussed, an example bone engagement feature may include hooks, spikes, and a modified or textured surface to enable the first end 401 and/or second end 405 of the implant 402 to engage with the vertebrae to prevent movement and migration. The surface may be modified or textured with etching, pores, or other features to provide a roughened surface for bone growth to engage the stabilization device. In some scenarios, a surface of one or more of the first vertebra and the second vertebra may be decorticated to prepare the vertebrae to receive the implant 402. The implant 402 may also be configured to be passively stabilized between the adjacent vertebra in response to pressure from surrounding ligaments, musculature, and tissue without an active fixation mechanism. While the bone fixation mechanisms and bone engagement features are described herein with respect to the implant 402 in the anterior configuration, similar fixation mechanisms and bone engagement features may be applied to the implant in the posterior configuration described below in conjunction with FIGS. 5A-D.

FIGS. 5A-5D illustrate example configurations of an inter-transverse process fusion device connecting transverse processes of adjacent vertebrae in a posterior configuration, arranged in accordance with at least some embodiments as described herein.

Figure 5A:
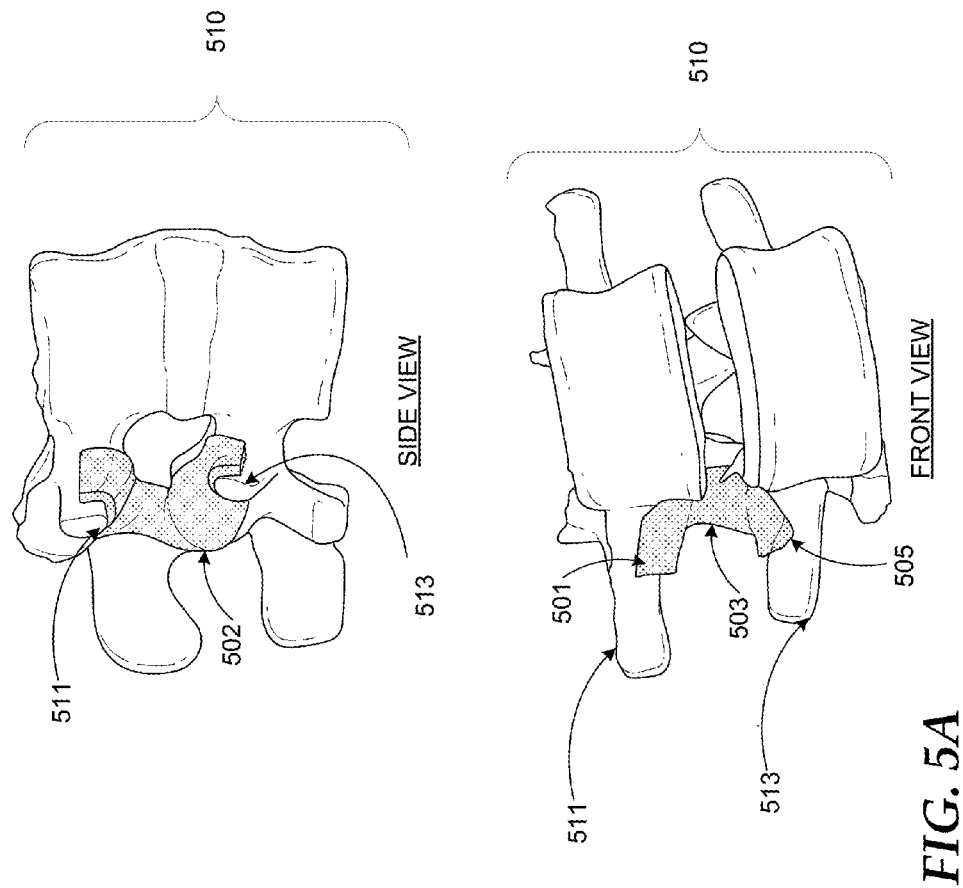
FIGS. 5A-5D illustrate example configurations of an inter-transverse fusion device connecting transverse processes of adjacent vertebrae in a posterior configuration.
Figure 5A:
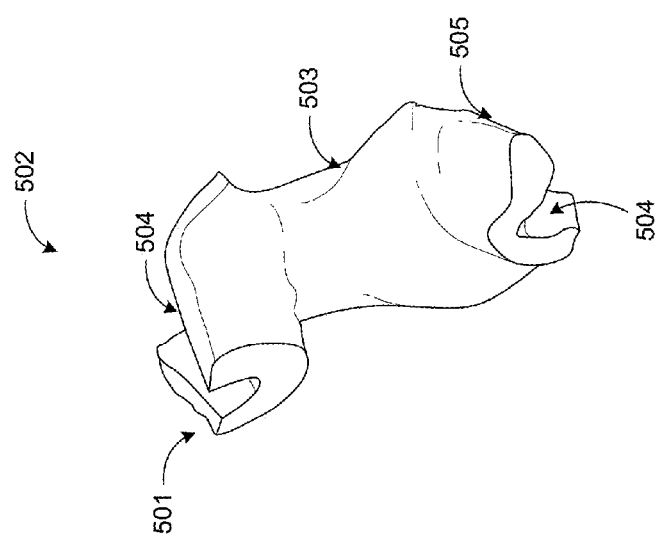

As discussed above, in conjunction with FIGS. 4A-4D, an inter-transverse process implant 502 may be inserted between transverse processes of an adjacent vertebral pair 510, with a first end 501 attached to a first transverse process 511 of an upper vertebra, a second end 505 attached to a second transverse process 513 of a lower vertebra, and a curved middle portion 503 extending between the first and second ends. As illustrated in FIG. 5A, the curved middle portion 503 may be in a posterior configuration with respect to the adjacent vertebral pair 510, such that the curved middle portion 503 may substantially follow a posterior anatomy of the adjacent vertebral pair 510 along facet joints.

A front view and a side view of the inter-transverse process implant 502 of FIG. 5A illustrates the inter-transverse process implant 502 inserted in position between the first transverse process 511 of the upper vertebra and the second transverse process 513 of the lower vertebra. The curved middle portion 503 may include a contoured channel 504 configured to receive portions of the bony anatomy between the upper and lower vertebra. When in position between the transverse processes (e.g., the first transverse process 511 and the second transverse process 513) of the vertebrae, the contoured channel 504 may be in contact with a portion of vertebral bone. As previously discussed, at least a portion of the bone contacting surface, including the contoured channel 504, may include a bone integration surface to promote bone ingrowth, on-growth, and/or through-growth with the implant 502.

Figure 5B:
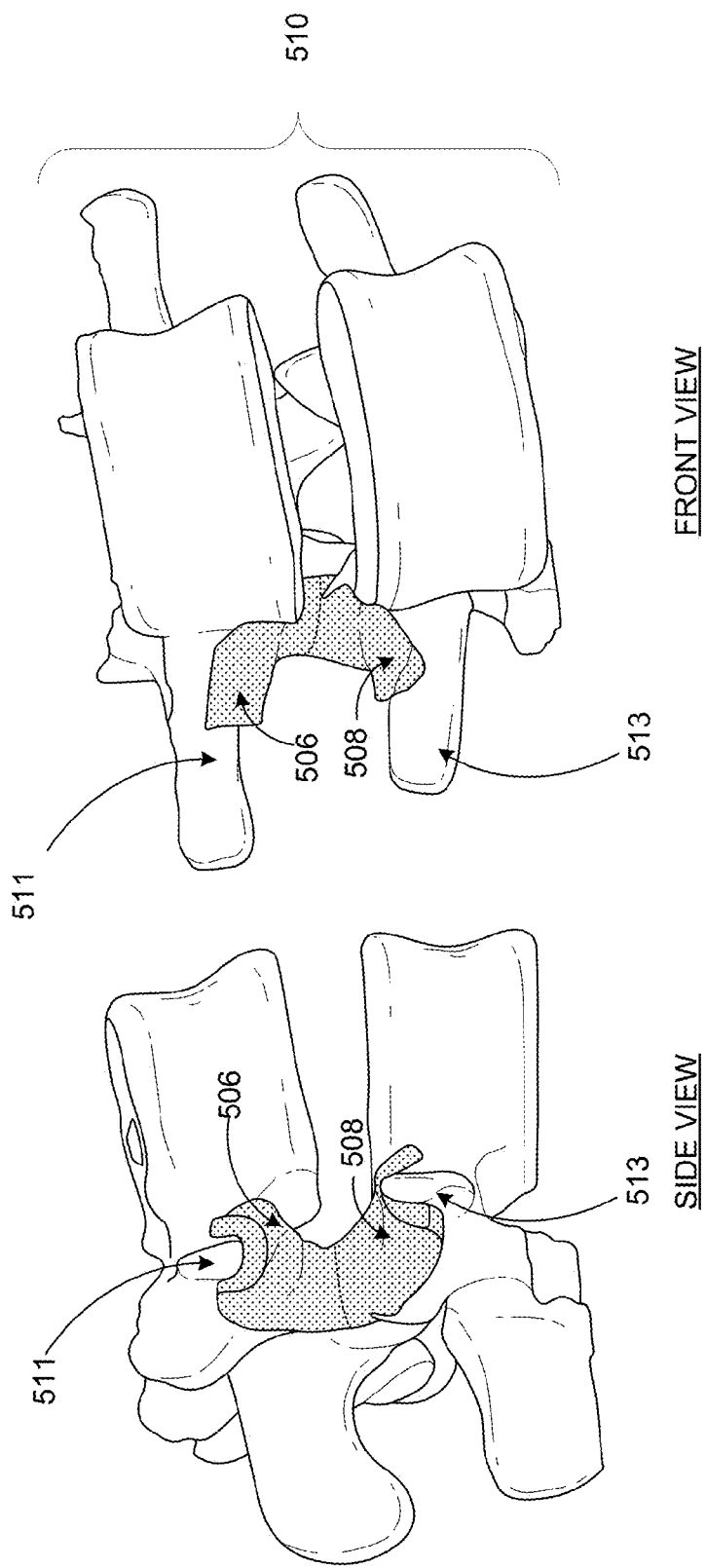

As illustrated in FIG. 5B, similar to the anterior configuration as previously described, the inter-transverse process implant 502 in the posterior configuration may include at least two portions to facilitate implantation, including an upper portion 506 and a lower portion 508. The upper portion 506 and lower portion 508 may be inserted separately, and may be coupled together in situ. For example, the upper portion 506 may be attached to a portion of the first transverse process 511 of the upper vertebra, and the lower portion 508 may be attached to a portion of the second transverse process 513 of the lower vertebra. After insertion of both the upper and lower portion, the upper portion 506 and the lower portion 508 may be coupled together through a coupling mechanism, such as a snap fit, a Morse taper engagement, connecting tabs, by screwing the portions together, by gluing the portions together with a biocompatible glue, or other similar coupling mechanism.

Figure 5C:
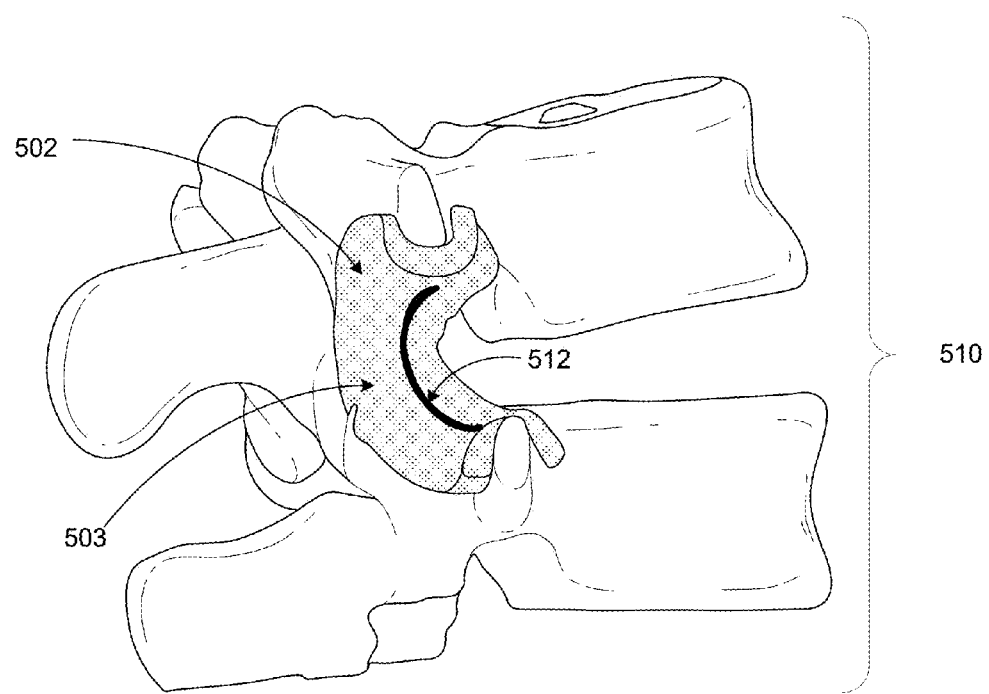

In another embodiment, as illustrated in FIG. 5C, a spring 512 may be incorporated with the inter-transverse process implant 502. While the spring 512 is shown integrated with the inter-transverse process implant 502 in the posterior configuration, the spring 512 may also be integrated with the curved middle portion of the inter-transverse process implant 502 in the anterior configuration. An example spring 512 may be curved to follow a shape of the curved middle portion 503 portion of the implant 502. The spring 512 may be a flexible and/or an expanding spring that allows the implant 502 to be flexible. In some embodiments, the spring 512 may be configured to mimic a flexibility and deformation of an intervertebral disc (not shown) between the adjacent vertebral pair 510. A flexibility of the spring may be dependent on a material and geometry of the spring 512. Additionally, a desired flexibility of the spring 512 may be achieved through incorporation of a dashpot with the spring 512. The spring 512 may be composed from a polymer material, a ceramic material, a metal or alloy material, such as nickel-titanium alloy or other similar shape memory alloy material, or a combination thereof.

In some embodiments, the spring 512 may be configured to compress the bone contacting channel 504 of the implant 502 against vertebrae to increase a surface area of the contoured channel 504 that is in contact with the surface of the vertebrae. The spring 512 may also be configured to apply a distraction force of a desired magnitude to facilitate fusion of the adjacent vertebral pair 510 in a desired position.

Figure 5D:
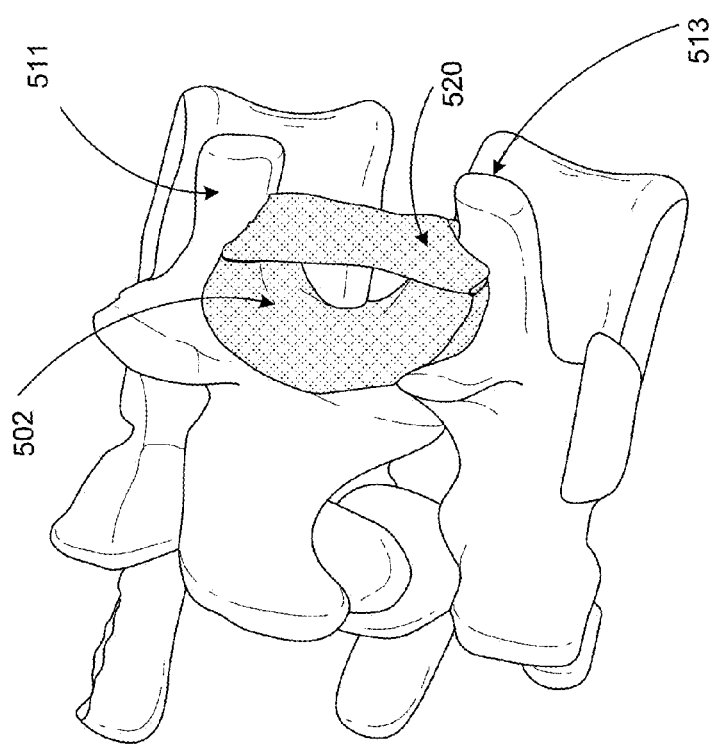

In a system according to embodiments, as illustrated in FIG. 5D, a supporting cross-member 520 may be integrated with the inter-transverse process implant 502. While the cross-member 520 as shown is integrated with the inter-transverse process implant 502 in the posterior configuration, the cross-member 520 may also be integrated with the inter-transverse process implant 502 in the anterior configuration. The cross-member 520 may be configured to connect the first end and the second end of the implant 502 and to extend across the transverse processes (e.g., the first transverse process 511 and the second transverse process 513) of the adjacent vertebrae to add strength and stability to the implant 502. The cross-member 520 may have varying dimensions to control rigidity as desired. Additionally, the cross-member 520 may be composed from materials having time dependent and non-isotropic properties that may allow the implant 502 to react according to a rate of loading as well as according to a direction of the load, which may provide a protective mechanism to the spine when excessive loads are applied. When an excessive load is applied to the spine, the load may be shared between the spine and the implant 502, with extra strength supplied via the supportive cross-member 520.

Similar to the spinal stabilization devices described herein, the inter-transverse process implant 502, in both posterior and anterior configurations, may be composed from a polymer, a metal, an alloy, or a combination thereof. Example polymer, metal, and alloy materials may be as described herein. Furthermore, at least a portion of the implant 502 may be treated or coated with a calcium material, as described herein, to enhance a strength of bone ingrowth, on-growth, and/or through-growth between the vertebrae and with the implant 502 by enabling newly forming bone to draw from the calcium deposits when forming.

In a further embodiment, example techniques for insertion and implantation of the inter-transverse process implant 502 may include an open surgical procedure and/or a minimally invasive surgical procedure, as described herein. An example procedure may include dissection and exposure to access a targeted vertebral pair and optional decortication of the receiving vertebral bone areas, such as the transverse processes. Subsequently, a first end, or an upper portion, of the implant 502 may be attached to an upper vertebra and the other end, and/or the lower portion, of the implant 502 may be attached to the lower vertebra as described above.

As previously described herein, the inter-transverse process implant may be customized for individuals based on a predetermined anatomy of each individual. For example, bone contacting portions of the device, such as the contoured channel between the first and second ends, may match a surface of the bone. Additionally, dimensions of the device may match a space between vertebrae where the inter-transverse process implant may be inserted.

FIGS. 6A-6G illustrate various configurations of a spinal fusion/fixation device including end saddles to connect transverse processes of adjacent vertebrae, arranged in accordance with at least some embodiments as described herein.

Figure 6A:
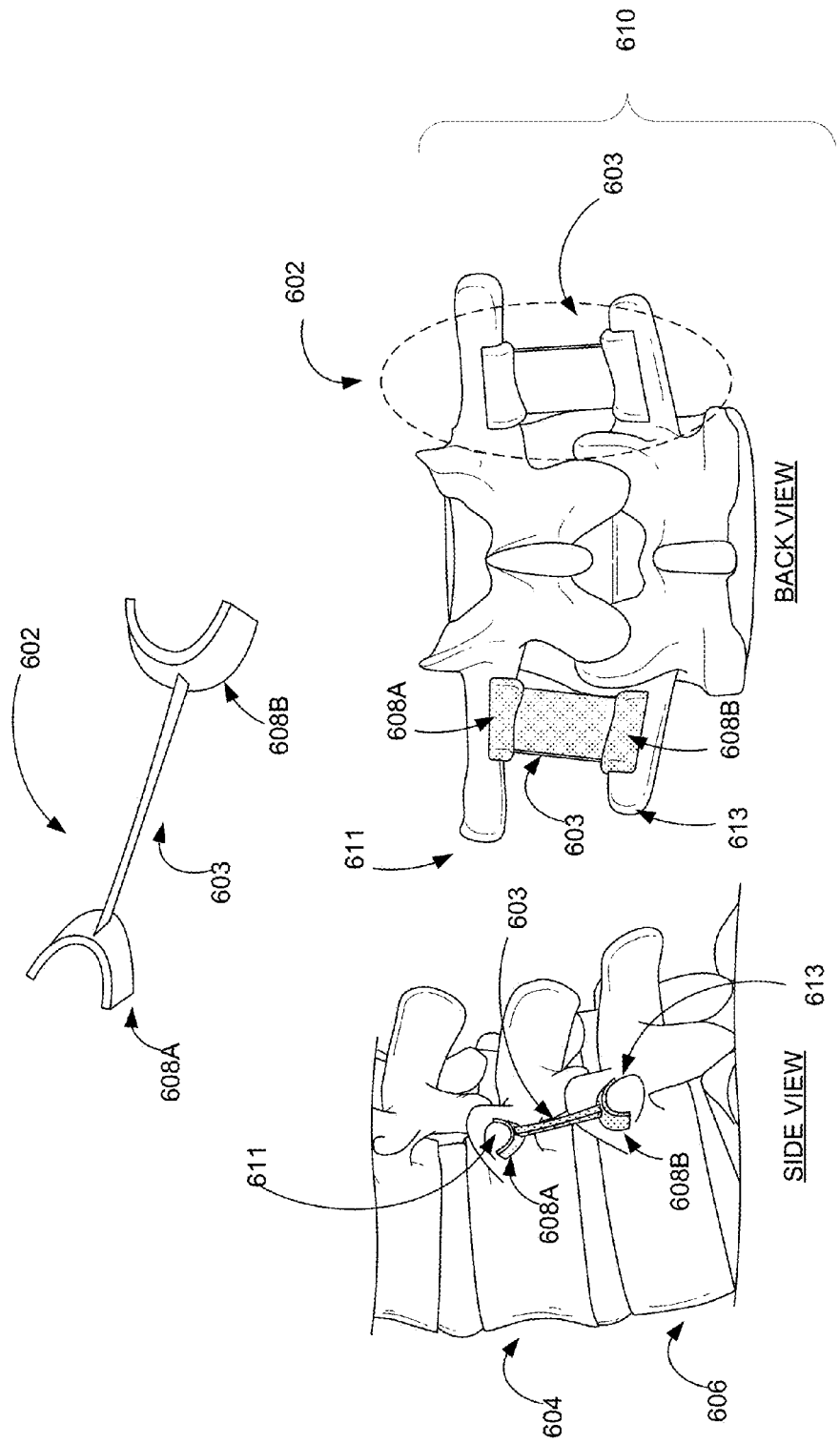
FIGS. 6A-6G illustrate various configurations of a spinal fusion/fixation device including end saddles to connect transverse processes of adjacent vertebrae.

As illustrated in FIG. 6A, a spinal stabilization device may be an inter-transverse process implant 602 configured to be inserted between transverse processes of an adjacent vertebral pair 610 (e.g., a first transverse process 611 of a first or upper vertebra 604 and a second transverse process 613 of a second or lower vertebra 606). The implant 602 may include a first end configured to be in contact with the first transverse process 611 of the upper vertebra 604, a second end configured to be in contact with the second transverse process 613 of the lower vertebra 606, and a middle portion 603 extending between the first end and the second end. In a system according to embodiments, as demonstrated in FIG. 6A, one or both of the first and second ends may include a curved portion (e.g., 608A and 608B) which may resemble a u-shape or a j-shape in a cross-sectional view or perspective, for example. The curved portions 608A and 608B may be adapted to be in contact with a portion of an upper vertebra 604 and/or lower vertebra 606 of the adjacent vertebral pair 610. The curved portions 608A and 608B may resemble a cup or a saddle, and may be configured to receive and rest on a transverse process of a vertebra. For example, a first curved portion 608A on the first end may be adapted to receive the first transverse process 611 of the upper vertebra 604, and a second curved portion 608B on the second end may be adapted to receive the second transverse process 613 of the lower vertebra 606.

As also illustrated in FIG. 6A, two implants may be inserted concurrently on a right and left side of a spine between an adjacent vertebral pair 610. In some embodiments, the length of the two middle portions 603 of each of the implants 602 may be equal to maintain an equal spacing between the adjacent vertebrae, while in other embodiments, the lengths of the middle portions 603 of each of the implants may be different, in order to compensate for a determined spacing misalignment between adjacent vertebrae. Dimensions, such as a shape and size, of the implant(s) 602 may be selected pre-operatively based on patient anatomy specifics, and desired results.

Figure 6B:
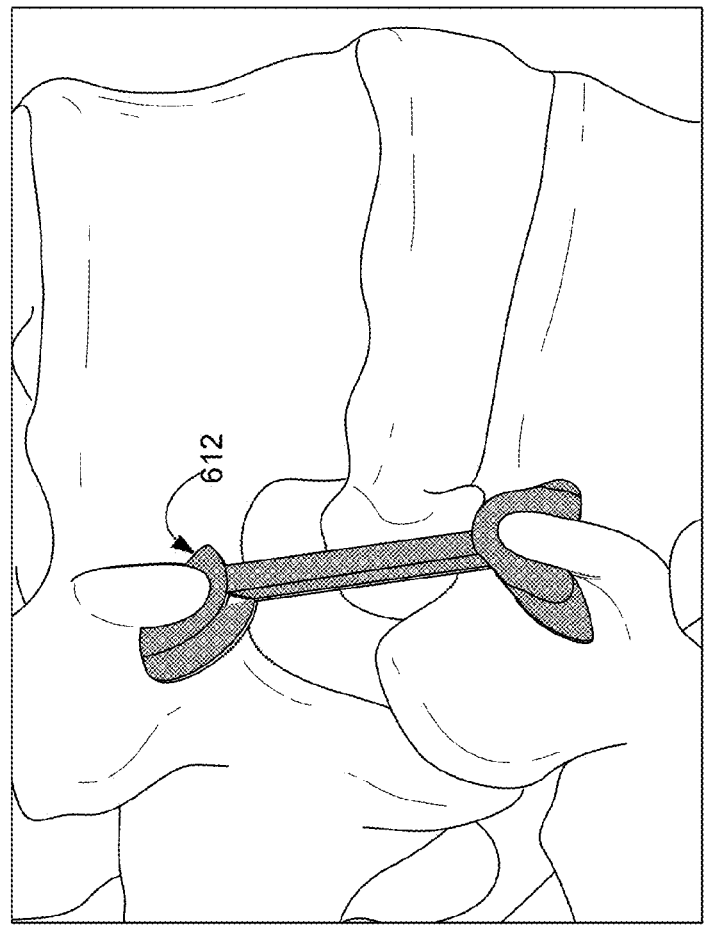
Figure 6B:
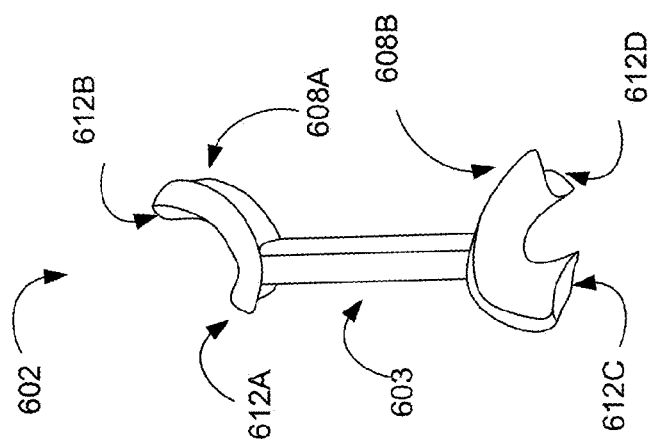

In a system according to embodiments, as illustrated in FIG. 6B, edges (e.g., edges 612A, 612B, 612C, and 612D) of each of the first curved portion 608A and the second curved portion 608B may be shortened to facilitate implantation. For example, an anterior edge of one or both of the curved portions may be shortened, and/or a posterior edge of one or both of the curved portions may be shortened.

Additionally, one or both of the first curved portion 608A and the second curved portion 608B may be mechanically anchored to the portion of the upper vertebra 604 and the lower vertebra 606 employing a mechanical fixation mechanism to stabilize the device in position and to prevent undesired movement and migration of the device once in position. Example fixation mechanisms may include screws, clamps, sutures, hooks, wires, roughened surfaces, and other similar fixation mechanisms. Furthermore, the first curved portion 608A and the second curved portion 608B may also include a bone engagement feature to prevent migration, such as hooks, spikes, and a modified or textured surface to enable the first curved portion 608A and/or the second curved portion 608B to engage with the vertebrae to prevent movement and migration. In other embodiments, the implant 602 may also be configured to be passively maintained in place between the adjacent vertebrae due to pressure from surrounding ligaments, musculature, and tissue without actively fixing the implant 602 employing a fixation mechanism.

Figure 6C:
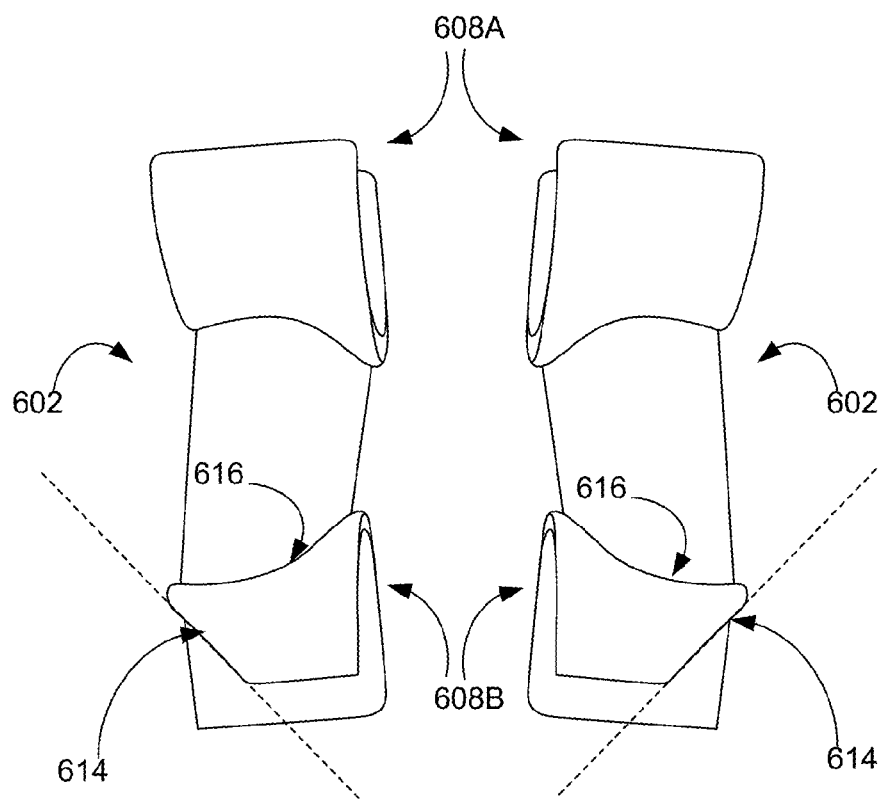
Figure 6D:
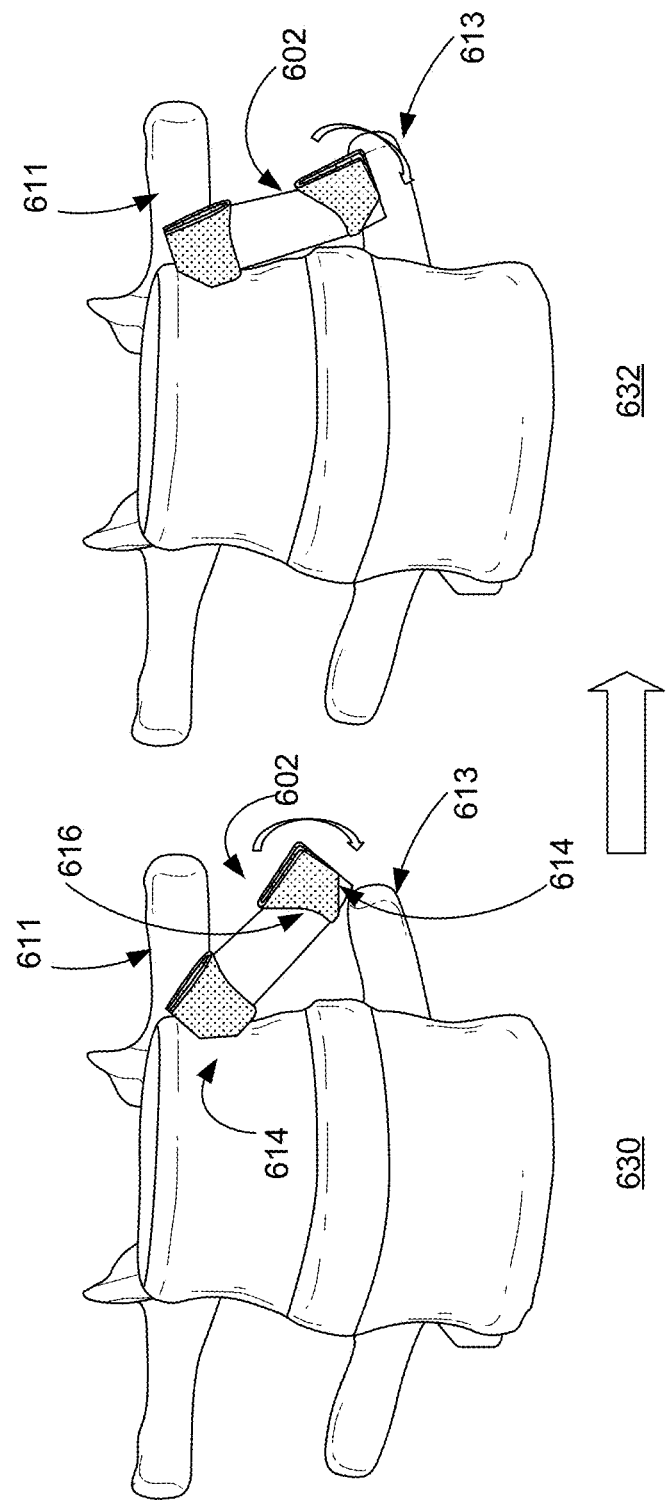

In another embodiment, as illustrated in FIG. 6C, the implant 602 may include one or more cutouts 614 to facilitate placement and implantation. The cutouts 614 may enable a rotational implant strategy to be applied, which may enable the implant 602 to be inserted between the adjacent vertebrae at a variety of angles, and rotated into a final desired position between the adjacent vertebrae. The cutaway portions may be pre-formed at one or both ends of the implant. Additionally, an arc 616 shape may be formed at a base of each of the curved portions 608A and 608B to allow the implant 602 to be rotated into place on a transverse process of the vertebra. As illustrated in FIG. 6D, the implant 602 may initially be inserted at an angle as shown in configuration 630, and the implant 602 may be rotated into a final position as shown in configuration 632 between the transverse processes (e.g., the first transverse process 611 and the second transverse process 613), by rotating the implant 602 around a pivot point with the cutouts 614 and arcs 616 of the curved portions 608 facilitating rotation and implantation without interference from the transverse processes.

Figure 6E:
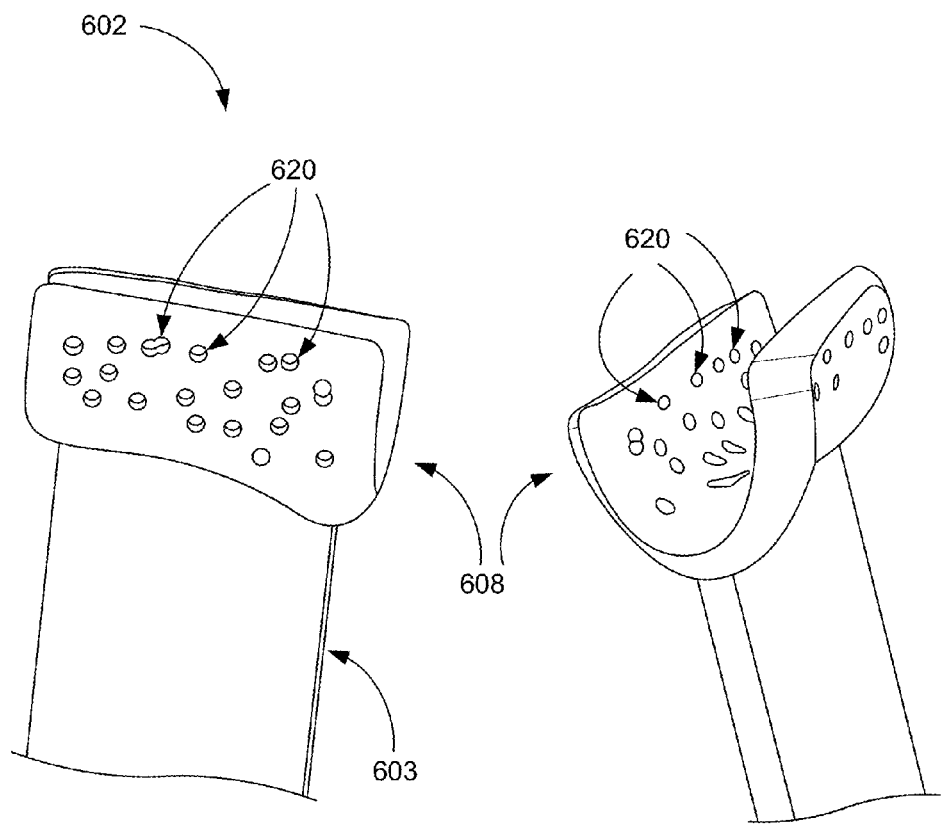

In a further embodiment, as illustrated in FIG. 6E, at least a portion of the device may include a bone integration surface to promote bone ingrowth, on-growth, and/or through-growth between the first vertebra, the second vertebra, and the implant 602 to facilitate fusion between the first vertebra and the second vertebra and/or to facilitate fusion between the implant 602 and one or both of the first and second vertebrae. The bone integration surface may include a plurality of perforations 620 formed in one or more of the first and second curved portions 608A and 608B and optionally also in the middle portion 603 between the first and second end of the implant. The plurality of perforations 620 may enable bone to grow into and/or completely through the implant. The plurality of perforations 620 may have a diameter in a range from about 100-300 µm to support bone ingrowth and on-growth. The size, shape, and number of perforations may vary over the implant.

As discussed herein, a bone integration surface of the implant 602 may also be achieved through the provision of an appropriate surface topography, for example a roughened or textured area and/or by the provision of osteoconductive coatings, such as calcium phosphates. The bone integration surface may enable the device to provide a metal and/or polymeric scaffold for tissue integration to be achieved through the device. Additionally, the bone integration surface may be present on one side of the implant 602 only, such as the bone contacting surface, so that there is no bony growth on the other side, which may prevent bone growth over nerves and other tissue. Furthermore, at least a portion of the implant 602 may be treated or coated with a calcium material, as described herein, to enhance a strength of bone ingrowth, on-growth, and/or through-growth between the vertebrae and with the implant. The coated calcium deposits may enable newly forming bone to draw from the calcium deposits when forming.

Figure 6F:
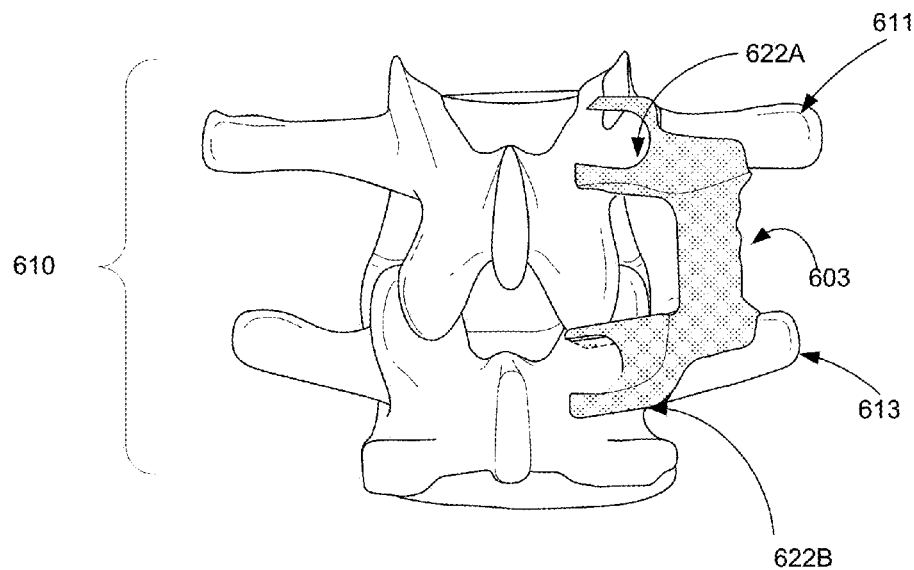
Figure 6F:
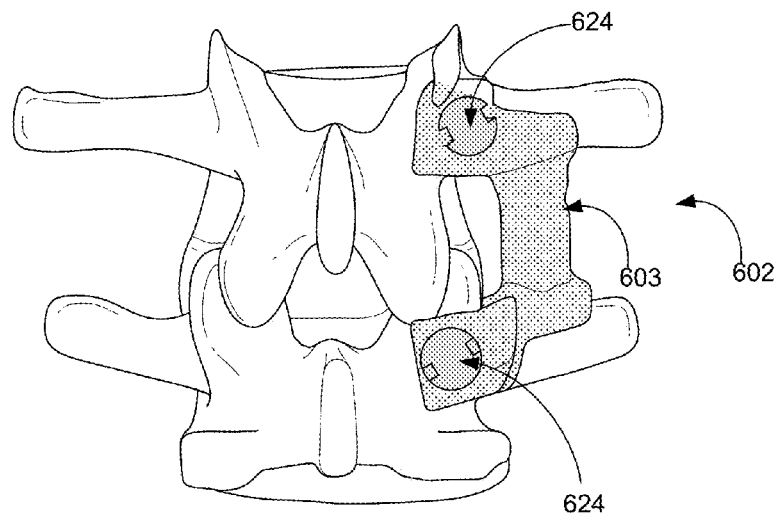
Figure 6G:
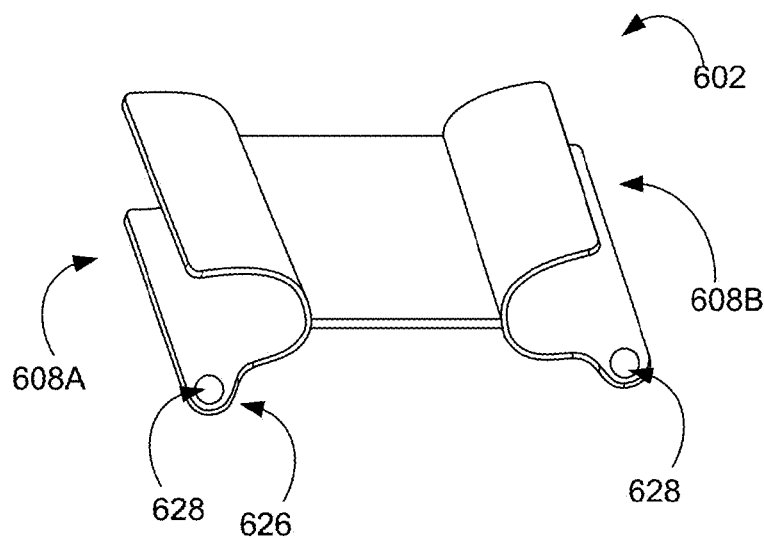
Figure 6G:
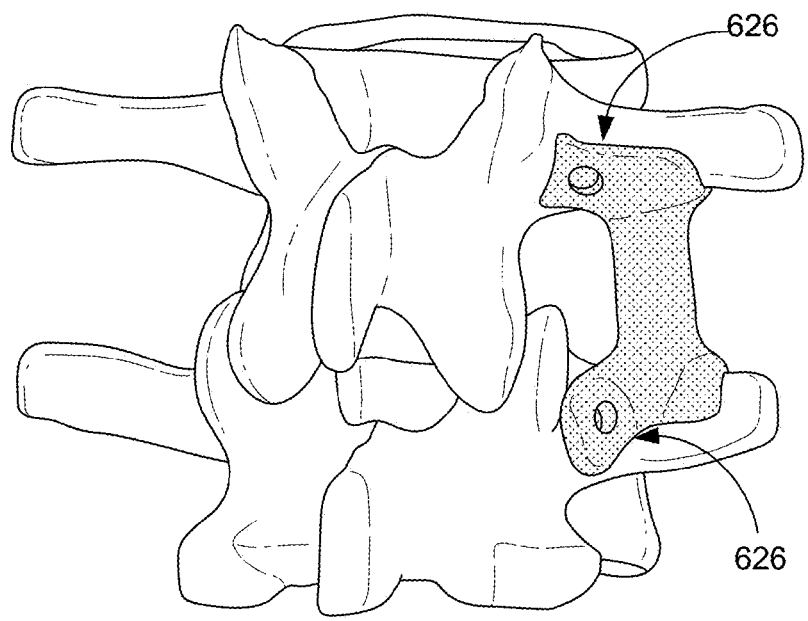

As illustrated in FIGS. 6F and 6G, in some embodiments, the implant 602 may be integrated with existing pedicle screw and/or rod systems incorporated within one or more vertebrae. In an example embodiment, at least one of the first end and the second end may include an attachment component (e.g., 622A and 622B) configured to facilitate integration of the implant 602 with an attachment mechanism, such as pedicle screw and/or rod systems. For example, the attachment components 622A and 622B may be a flange configured to connect the middle portion 603 of the implant 602 with a pedicle screw inserted within a pedicle of the first and/or second vertebra of an adjacent vertebral pair 610. In another embodiment, the attachment component(s) 622A and 622B may enable incorporation of the implant 602 with pedicle screw and rod systems where the implant 602 may interconnect with a structure of the pedicle screw, such as a saddle portion of a monoblock or a multi-axial pedicle screw, which may also involve the implant 602 to incorporate a rod portion. Additionally, the attachment component 622 may include one or more lugs 624 to interconnect with pedicle screws, or one or more tabs placed on either side of a pedicle screw.

FIG. 6G illustrates example tabs 626 extending laterally from a portion of the curved portions 608A and 608B of the implant 602. Example tabs 626 may provide temporary stabilization to prevent movement and migration while fusion forms. Additionally, the tabs 626 may be deformed upon insertion and may fix closely to inserted pedicle screws to provide additional stability. The tabs may include holes 628 to enable integration with an attachment mechanism. In some examples, the holes 628 may have a two dimensional taper configured to lock the pedicle screws within the hole by slight force and deformation.

In an example embodiment, example techniques for insertion and implantation of the inter-transverse process implant 602 may include an open surgical procedure and/or a minimally invasive surgical procedure, as described herein. An example procedure may include dissection and exposure to access a targeted vertebral pair and preparation of the receiving vertebral bone areas, such as the transverse processes. Subsequently, a first end, or an upper portion, of the implant 602 may be attached to an upper vertebra 604 and the other end, and/or the lower portion, of the implant 602 may be attached to the lower vertebra 606 as described above.

An example bone preparation may involve a vibrational bone preparation technique where a textured, roughened, or sharpened surface may be used to prepare a portion of vertebral bone by scratching, bruising, or otherwise eliciting a healing response from the bone and/or periosteum (i.e., a membrane that covers the outer surface of the bone). The vibrational preparation technique may employ surfaces having various levels of texture or roughness, and may be applied at varying intensity levels to produce a desired effect. For example, a less rough surface with mild vibration may be employed to bruise periosteum alone or together with bone tissue, or bone tissue alone where the periosteum has been removed and bone exposed due to a previously performed procedure. Higher levels of roughness and vibration may be used to broach the tissue, shaping it and allowing access to internal bone tissue, such as marrow elements.

As previously described herein, the inter-transverse process implant may be customized for individuals based on a predetermined anatomy of each individual. For example, bone contacting portions of the device, such as the curved portions on the first and second ends, may be manufactured to match a surface of the bone as determined by detailed anatomy scans of an individual. Additionally, dimensions of the device may match a space between vertebrae where the inter-transverse process implant may be inserted.

Figure 7:
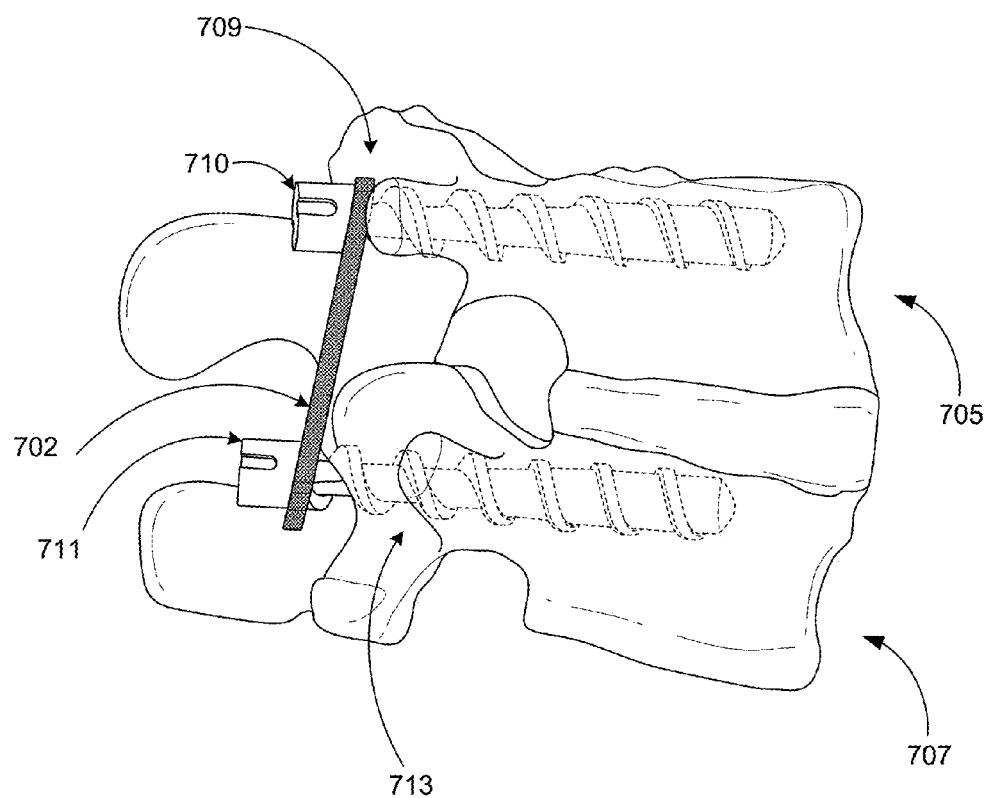
FIG. 7 illustrates a plate fixation device to connect pedicle screws inserted in adjacent vertebrae, all arranged in accordance with at least some embodiments as described herein.
Figure 7:
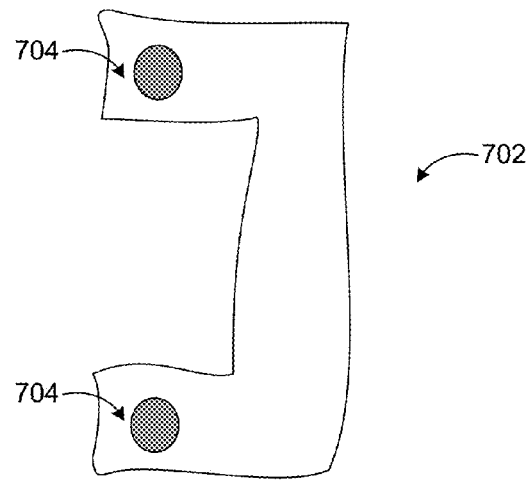

FIG. 7 illustrates a plate fixation device 702 to connect pedicle screws inserted in adjacent vertebrae, arranged in accordance with at least some embodiments as described herein. The plate fixation device 702 may be an elongated plate configured to extend between a first pedicle screw 710 inserted within a first vertebra 705 and a second pedicle screw 711 inserted within a second vertebra 707 of an adjacent vertebral pair. The plate fixation device 702 may include one or more attachment components 704, which may be holes, configured to accommodate insertion of the first and/or the second pedicle screws 710 and 711. The attachment components 704 may include a locking mechanism to accommodate coupling with the first pedicle screw 710 and/or the second pedicle screw 711 such that when the first pedicle screw 710 and/or the second pedicle screw 711 is inserted within the one or more holes, the plate fixation device 702 may be compressed against the first vertebra 705 and the second vertebra 707. Other example locking mechanisms may lock specialized attachment components 704 into the surface of the plate and the first pedicle screw 710 and/or the second pedicle screw 711 without limitations of thread profiles. The attachment components 704 may also feature a non-locking design where the attachment component 704 may enable the first pedicle screw 710 and/or the second pedicle screw 711 to couple to the plate without loading the vertebra and transferring a load to the first pedicle screw 710 and/or the second pedicle screw 711.

In some embodiments, at least a portion of the plate fixation device 702 may include a bone integration surface to promote bone ingrowth, on-growth, and/or through-growth between the first vertebra, the second vertebra, and the plate fixation device 702 to facilitate fusion between the first vertebra 705 and the second vertebra 707 and/or to facilitate fusion between the plate fixation device 702 and one or both of the first and second vertebrae. While embodiments have been discussed above using specific examples, components, and configurations, they are intended to provide a general guideline to be used for devices, systems, and methods to provide spinal fixation, spinal stabilization, and/or spinal fusion. These examples do not constitute a limitation on the embodiments, which may be implemented using other components, modules, and configurations using the principles described herein. Furthermore, actions discussed above may be performed in various orders, especially in an interlaced fashion.

The present disclosure describes a spinal stabilization device to facilitate spinal fusion. The spinal stabilization device may include an inter-transverse process implant including a first end including a first curved portion adapted to be in contact with a portion of a first vertebra of an adjacent vertebral pair, a second end including a second curved portion adapted to be in contact with a portion of a second vertebra adjacent to the first vertebra, and a middle portion extending between the first end and the second end, at least a portion of the middle portion adapted to be positioned between the first vertebra and the second vertebra.

According to some embodiments, first curved portion may define a channel that may be adapted to receive a first transverse process of the first vertebra, and the second curved portion may define a channel that may be adapted to receive a second transverse process of the second vertebra. One or both edges of each of the first and second curved portions may be shortened to facilitate implantation.

According to some embodiments, one or both of the first end and the second end include a cutaway portion to enable the device to be inserted between the adjacent vertebral pair and rotated into a final position between the first vertebra and the second vertebra. At least one of the first end and the second end includes an attachment component configured to facilitate fixation of the inter-transverse process implant with the first and second vertebrae.

According to other embodiments, the attachment component may comprise an opening configured to receive a screw therethrough to connect the inter-transverse process implant to one or more of the first vertebra and/or the second vertebra. The attachment component may extend laterally from one of the first end and the second end. The attachment component may be arranged to receive a screw for insertion within at least a portion of a pedicle of the first vertebra and/or the second vertebra when the first and second ends may be engaged with respective first and second transverse processes.

According to other embodiments, the middle portion may be configured in a substantially curved shape in one of a posterior or an anterior configuration with respect to the adjacent vertebral pair. The middle portion of the inter-transverse process implant includes a channel along a bone contacting surface.

According to some embodiments, in an anterior configuration, the middle portion of the inter-transverse process implant may be configured to substantially follow an anterior aspect of a foramen of the adjacent vertebral pair. Additionally, in the anterior configuration, a channel of the middle portion may be contoured to accommodate a natural bony anatomy of vertebral bodies of the adjacent vertebral pair and an intervertebral disk between the first vertebra and the second vertebra.

According to other embodiments, in the posterior configuration, a channel of the middle portion may be contoured to accommodate a natural bony anatomy of a posterior portion along a facet joint of the first vertebra and the second vertebra.

According to some embodiments, the implant may also include a spring configured to follow the curved shape of the middle portion. The spring may be configured to press a bone contacting surface of the inter-transverse process implant against the first vertebra and the second vertebra. The spring may be configured to induce a distraction force between the first vertebra and the second vertebra.

According to some embodiments, at least one of the first curved portion, the second curved portion, and the middle portion includes a bone integration surface on at least one side thereof to promote bone ingrowth, on-growth, and/or through-growth between the first vertebra and the second vertebra to facilitate fusion between the first vertebra and the second vertebra. The bone integration surface comprises a textured surface and/or a plurality of perforations. Each of the plurality of perforations have a diameter in a range from about 100 micrometers to about 300 micrometers.

According to some embodiments, the implant may also include a stabilizing cross member configured to extend from the first end to the second end to enhance a strength and stability of the inter-transverse process implant between the first vertebra and the second vertebra. At least one of the first end and the second end includes a bone engagement feature. The bone engagement feature may be configured to induce a bone healing response in one of the first vertebra or the second vertebra.

According to other embodiments, the inter-transverse process implant may be configured to be stabilized between the first vertebra and the second vertebra in response to pressure from surrounding ligaments, musculature and tissue. One or more of the first end, the second end, and the middle portion may be composed from one or more of: a polymer, a metal, and an alloy.

According to further embodiments, one or more of the first end and the second end may be configured to be affixed to a portion of the first vertebra and second vertebra employing a fixation mechanism, where the fixation mechanism may be selected from one or more of a screw, a clamp, a suture, a hook, a spike, a textured surface, and a wire. One or more of the first end and the second end may be configured to be affixed to a vertebral body of the first and second vertebra.

According to further embodiments, inter-transverse process implant may include at least two parts including an upper portion and a lower portion, the upper portion and the lower portion configured to be coupled together after insertion between the first vertebra and the second vertebra. The upper portion and the lower portion may be configured to be coupled together employing one or more of: a snap fit, a Morse taper engagement, a screw fixation, a tab fixation, or a glue.

According to other embodiments, a portion of the inter-transverse process implant may be coated with a calcium deposit material to enable newly forming bone to draw from the calcium deposit material.

The present disclosure also describes a spinal stabilization device to facilitate spinal fusion, including a first end adapted to be in contact with a first vertebra of an adjacent vertebral pair, a second end adapted to be in contact with a second vertebra of the adjacent vertebral pair, and a middle portion extending between the first end and the second end, at least a portion of the middle portion adapted to be positioned between the first vertebra and the second vertebra. The first vertebra may be a relatively superior vertebra and the second vertebra may be a relatively inferior vertebra of the adjacent vertebral pair.

According to some embodiments, at least one of the first end and the second end may be bifurcated, the bifurcated end configured to straddle a portion of one of the first vertebra or the second vertebra. At least a portion of the bifurcated second end may be positioned within a facet joint between the second vertebra and the first vertebra. The bifurcated second end may be configured to straddle a superior articular process of the second vertebra such that at least a portion of the bifurcated second end may be positioned within the facet joint between the second vertebra and the first vertebra.

According to other embodiments, one or more of the first end and the second end includes a channel configured to receive one of: a pedicle, a transverse process, or a superior articular process of the first vertebra. One or more of the first end and the second end may be configured to be affixed to a portion of the first vertebra employing a fixation mechanism. The fixation mechanism may be selected from one or more of a screw, a clamp, a suture, a hook, and a wire.

According to other embodiments, one or more of the first end and the second end may be configured to be affixed to one of: a pedicle, a transverse process, or a superior articular process of the first vertebra. One or more of the first end, the second end, and the middle portion includes a bone engagement feature, the bone engagement feature including one or more of: a fastener, a roughened surface, a plurality of spikes, and a plurality of hooks. The bone engagement feature may be configured to induce a bone healing response in one of the first vertebra or the second vertebra.

According to further embodiments, the middle portion may be curved from the first end to the second end to substantially follow a natural bony anatomy between the first vertebra and the second vertebra. The middle portion may be configured to apply an expansion force between the first end and the second end. The middle portion may be configured to extend between the first end and the second end across lamina of the adjacent vertebral pair. The middle portion may be configured to extend between the first end and the second end across vertebral bodies of the adjacent vertebral pair.

According to further embodiments, the spinal stabilization device may be an elongated plate, the elongated plate configured to extend between the first vertebra and the second vertebra of the adjacent vertebral pair such that the first end of the plate may be in contact with a posterior lamina of the first vertebra, and the second end of the plate may be in contact with a posterior lamina of the second vertebra. The middle portion of the plate may be contoured to substantially follow a natural bony anatomy of a posterior portion of the adjacent vertebral pair.

According to some other embodiments, the device may also include a locking component configured to extend from the plate into a facet joint between the first vertebra and the second vertebra. The locking component may be a hook configured to insert within the facet joint to stabilize the plate in position between the first vertebra and the second vertebra.

According to other embodiments, one or more of the first end and the second end may be configured to be affixed to the posterior lamina of the first and second vertebra employing a fixation mechanism, where the fixation mechanism may be selected from one or more of a screw, a clamp, a suture, a hook, a spike, a textured surface, and a wire. One or more of the first end, the second end, and the middle portion includes a bone integration surface configured to promote bone ingrowth, on-growth, and/or through-growth between the first vertebra and the second vertebra to facilitate fusion between the first vertebra, the second vertebra and/or the spinal stabilization device.

According to other embodiments, a portion of the spinal stabilization device may be coated with a calcium deposit material to enable newly forming bone to draw from the calcium deposit material. The spinal stabilization device may be configured to be stabilized between the first vertebra and the second vertebra in response to pressure from surrounding ligaments, musculature and tissue.

According to some other embodiments, At least a portion of the spinal stabilization device may be composed from one or more of: a polymer, a metal, and an alloy. The metal may be selected from one or more of: titanium, titanium alloy, stainless steel, cobalt-chromium alloy, and tantalum. The polymer may be selected from one or more of: polyetheretherketone (PEEK), polyethylene (PE), modified PEEK, modified PE and biodegradable polymers.

The present disclosure also describes a spinal stabilization device to facilitate spinal fusion, including a plate fixation device configured to extend between a first pedicle screw inserted within a first vertebra and a second pedicle screw inserted within a second vertebra, where the plate fixation device includes one or more holes configured to accommodate insertion of the first and/or the second pedicle screws. The plate fixation device may include a locking mechanism to accommodate coupling with the first and/or the second pedicle screw such that when the first and/or the second pedicle screw may be inserted within the one or more holes, the plate fixation device may be compressed against the first vertebra and the second vertebra.

The present disclosure further describes a method to achieve spinal fusion, including inserting a spinal stabilization device between an adjacent vertebral pair such that a first end of the spinal stabilization device may be in contact with a first vertebra of the adjacent vertebral pair, and a bifurcated second end of the spinal stabilization device may be in contact with a second vertebra of the adjacent vertebral pair such that the bifurcated second end straddles a portion of the second vertebra.

The method may include positioning the bifurcated second end such that the bifurcated second end straddles a superior articular process of the second vertebra. The method may also include positioning at least a portion of the bifurcated second end within a facet joint between the second vertebra and the first vertebra.

According to some embodiments, the method may include contacting the first end with the first vertebra such that a channel formed on a bone-contacting side of the first end may be configured to receive one of: a pedicle, a transverse process, or a superior articular process of the first vertebra. The method may include implanting the spinal stabilization device extraosseously such that the first end rests upon the first vertebra and the second end rests upon the second vertebra without active fixation. The method may include affixing the first end to a portion of the first vertebra employing a fixation mechanism, where the fixation mechanism may be selected from one or more of a screw, a clamp, a suture, a hook, and a wire vertebra.

According to some embodiments, the method may include preparing a surface of one or more of the first vertebra and the second vertebra to receive the spinal stabilization device prior to insertion of the spinal stabilization device by one or more of: piercing a periosteum and decorticating the surface of one or more of the first vertebra and the second vertebra prior to insertion of the spinal stabilization device.

According to some embodiments, the method may include inserting the spinal stabilization device via an open procedure, where the open procedure includes dissection and exposure to access a targeted facet joint, and removal of a portion of cartilage within the targeted facet joint. The method may include inserting the spinal stabilization device via one or more of a posterior and a lateral approach.

The present disclosure also describes a method to achieve spinal fusion, including inserting an elongated plate between an adjacent vertebral pair, such that a first end of the plate may be in contact with a posterior lamina of a first vertebra of the adjacent vertebral pair, and a second end of the plate may be in contact with a posterior lamina of the second vertebra, and where a middle portion of the plate extending between the first end and the second end may be adapted to be positioned between the first vertebra and the second vertebra.

According to some embodiments, the method may include positioning the plate such that a locking component extending from a portion of the plate may be inserted into a facet joint between the first vertebra and the second vertebra. The method may also include affixing one or more of the first end and the second end to the posterior lamina of the first and second vertebra employing a fixation mechanism, where the fixation mechanism may be selected from one or more of a screw, a clamp, a suture, a hook, a spike, a textured surface, and a wire. The method may also include selecting one or more of a shape, a size, and a contour of the plate to substantially follow a natural bony anatomy of a posterior portion of the adjacent vertebral pair. The method may also include after insertion of the plate in position between the first vertebra and the second vertebra, modifying a shape and a contour of the plate.

According to some embodiments, the method may include inserting the plate via one or more of a posterior and a lateral approach. The method may also include preparing a surface of one or more of the first vertebra and the second vertebra to receive the plate prior to insertion of the plate by decorticating the surface of one or more of the first vertebra and the second vertebra prior to insertion of the plate.

According to other embodiments, the method may include treating at least a portion of the plate to enhance a bone integration surface of the plate, where the bone integration surface may be configured to promote bone ingrowth, on-growth, and/or through-growth between the first vertebra and the second vertebra to facilitate fusion between the first vertebra and the second vertebra. Treating at least a portion of the plate further may include texturizing and/or etching a surface of the plate to induce a roughness, coating a surface of the plate with a porous material, coating a surface of the plate with a titanium coating, and coating a surface of the plate with a plasma spray.

The present disclosure further describes a method to achieve spinal fusion, including inserting an inter-transverse process implant between a first vertebra and a second vertebra of an adjacent vertebral pair such that a first end of the implant may be in contact with a first transverse process of the first vertebra of the adjacent vertebral pair, a second end of the implant may be in contact with a second transverse process of the second vertebra of the adjacent vertebral pair, and a middle portion configured in a substantially curved shape extends between the first end and the second end in one of a posterior or an anterior configuration with respect to the adjacent vertebral pair.

According to some embodiments, the method may include positioning the implant such that, in the anterior configuration, the middle portion of the implant substantially follows an anterior aspect of a foramen of the adjacent vertebral pair.

The method may also include positioning the implant such that, in the posterior configuration, the middle portion of the implant substantially follows a posterior aspect of a foramen of the adjacent vertebral pair.

According to other embodiments, the method may include inserting the implant as separate upper and lower portions, where the upper portion and the lower portion may be configured to be coupled together after insertion between the first vertebra and the second vertebra. The method may also include affixing one or more of the first end and the second end to a portion of the first vertebra and the second vertebra employing a fixation mechanism, where the fixation mechanism may be selected from one or more: of a screw, a clamp, a suture, a hook, a spike, a textured surface, and a wire. The method may also include inserting the implant via one or more of a posterior and a lateral approach.

According to further embodiments, the method may include preparing a surface of one or more of the first vertebra and the second vertebra to receive the implant prior to insertion of the implant by decorticating the surface of one or more of the first vertebra and the second vertebra prior to insertion of the implant.

The method may also include treating at least a portion of the implant to enhance a bone integration surface of the implant, where the bone integration surface may be configured to promote bone ingrowth, on-growth, and/or through-growth between the first vertebra and the second vertebra to facilitate fusion between the first vertebra and the second vertebra. Treating at least a portion of the implant further may include texturizing and/or etching a surface of the implant to induce a roughness, coating a surface of the implant with a porous material, coating a surface of the implant with a titanium coating, and coating a surface of the implant with a plasma spray.

The present disclosure further describes a method to achieve spinal fusion, including inserting an inter-transverse process implant between a first vertebra and a second vertebra of an adjacent vertebral pair such that a first end including a first curved portion may be in contact with a portion of a first vertebra of an adjacent vertebral pair, a second end including a second curved portion may be in contact with a portion of a second vertebra adjacent to the first vertebra, and a middle portion coupling the first end and the second end extends between the first vertebra and the second vertebra.

According to further embodiments, the method may include inserting the implant such that the first curved portion receives a first transverse process of the first vertebra, and the second curved portion receives a second transverse process of the second vertebra. The method may also include, after initial insertion of the implant between the first vertebra and the second vertebra, rotating the implant into a final position between the first vertebra and the second vertebra.

According to other embodiments, the method may include integrating an attachment component of the implant with one or more pedicle screws inserted within a pedicle of the first vertebra and/or the second vertebra. The method may further include inserting the implant via one or more of a posterior and a lateral approach.

According to some other embodiments, the method may include treating at least a portion of the implant to enhance a bone integration surface of the implant, where the bone integration surface may be configured to promote bone ingrowth, on-growth, and/or through-growth between the first vertebra and the second vertebra to facilitate fusion between the first vertebra and the second vertebra. Treating at least a portion of the implant may further include texturizing and/or etching a surface of the implant to induce a roughness, coating a surface of the implant with a porous material, coating a surface of the implant with a titanium coating, and coating a surface of the implant with a plasma spray.

The present disclosure further describes a method to increase stability of an adjacent vertebral pair of a spine. The method may include selecting a spinal stabilization device having dimensions and mechanical parameters to achieve the increase in stability between the adjacent vertebral pair, preparing a portion of a surface of a first vertebra and a second vertebra of the adjacent vertebral pair employing a vibrational technique to receive the spinal stabilization device, and implanting the spinal stabilization device at a location relative to the adjacent vertebral pair.

According to some embodiments, the method may include promoting a fusion between the adjacent vertebral pair, where the fusion occurs through bone integration with the spinal stabilization device. Preparing the portion of the surface of the first vertebra and the second vertebra employing a vibrational technique may include applying a device having one of: a textured, roughened, and/or sharpened surface to the portion of the surface of the first vertebra and the second vertebra, and causing the device to vibrate over a range of intensities.

According to other embodiments, the method may include scratching, etching, texturizing, and/or bruising the surface of the portion of the surface of the first vertebra and the second vertebra to induce a bone healing response in the surface of the first vertebra and the second vertebra. The method may include employing a high vibration intensity to allow access to marrow elements of the first vertebra and the second vertebra.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various compositions, methods, systems, and devices are described in terms of "comprising" various components or steps (interpreted as meaning "including, but not limited to"), the compositions, methods, systems, and devices can also "consist essentially of" or "consist of" the various components and steps, and such terminology should be interpreted as defining essentially closed-member groups.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A spinal stabilization device coated in a material to facilitate spinal fusion, the spinal stabilization device comprising:
an inter-transverse process implant including:
a first end that includes a first curved portion in one of a u-shape or a j-shape in a cross-sectional view adapted to be in contact with a portion of a first vertebra of an adjacent vertebral pair, wherein:
the first curved portion includes a first anterior edge of a first length and a first posterior edge of a second length, and
the first anterior edge includes a first cutout;
a second end that includes a second curved portion in one of the u-shape or the j-shape in the cross-sectional view adapted to be in contact with a second vertebra portion, the second vertebra portion being adjacent to the first vertebra, wherein:
the second curved portion includes a second anterior edge of a third length and a second posterior edge of a fourth length,
the second anterior edge includes a second cutout, and
the first cutout and the second cutout enable a rotational insertion to occur to insert the inter-transverse process implant between the first vertebra and the second vertebra such that the first curved portion straddles a first transverse process of the first vertebra and the second curved portion straddles a second transverse process of the second vertebra;
a middle portion that extends between the first end and the second end, at least a portion of the middle portion adapted to be positioned between the first vertebra and the second vertebra; and
a stabilizing cross member, wherein the stabilizing cross member is configured to:
extend from the first end to the second end to enhance a strength and a stability of the inter-transverse process implant between the first vertebra and the second vertebra.

2. The spinal stabilization device of claim 1, wherein the middle portion includes a bone integration surface on at least one side thereof to promote one or more from a set of bone ingrowth, on-growth, and through-growth between the first vertebra and the second vertebra to facilitate fusion between the first vertebra and the second vertebra.

3. The spinal stabilization device of one of claim 2, wherein the bone integration surface comprises one or more from a set of a textured surface and perforations.

4. The spinal stabilization device of claim 3, wherein each of the perforations have a diameter in a range from about 100 micrometers to about 300 micrometers.

5. The spinal stabilization device of claim 1, further comprising:
a spring configured to follow a curved shape of the middle portion.

6. The spinal stabilization device of claim 5, wherein the spring is configured to press a bone contacting surface of the inter-transverse process implant against the first vertebra and the second vertebra.

7. The spinal stabilization device of claim 1, wherein:
the first curved portion defines a channel that is adapted to receive the first transverse process of the first vertebra, and
the second curved portion defines the channel that is adapted to receive the second transverse process of the second vertebra.

8. The spinal stabilization device of claim 1, wherein the middle portion is configured in a substantially curved shape in one from a set of a posterior and an anterior configuration with respect to the adjacent vertebral pair.

9. The spinal stabilization device of claim 1, wherein the middle portion of the inter-transverse process implant includes a channel along a bone contacting surface.

10. A spinal stabilization device coated in a material to facilitate spinal fusion, the spinal stabilization device comprising:
an inter-transverse process implant including:
a first end that includes a first curved portion in one of a u-shape or a j-shape in a cross-sectional view adapted to be in contact with a portion of a first vertebra of an adjacent vertebral pair, wherein:
the first curved portion includes a first anterior edge of a first length and a first posterior edge of a second length, and
the first anterior edge includes a first cutout;
a second end that includes a second curved portion in one of the u-shape or the j-shape in the cross-sectional view adapted to be in contact with a second vertebra of the adjacent vertebral pair, wherein:
the second curved portion includes a second anterior edge of a third length and a second posterior edge of a fourth length,
the second anterior edge includes a second cutout, and
the first cutout and the second cutout enable a rotational insertion to occur to insert the inter-transverse process implant between the first vertebra and the second vertebra such that the first curved portion straddles a first transverse process of the first vertebra and the second curved portion straddles a second transverse process of the second vertebra;
a middle portion that extends between the first end and the second end, at least a portion of the middle portion adapted to be positioned between the first vertebra and the second vertebra; and
a stabilizing cross member, wherein the stabilizing cross member is configured to:
extend from the first end to the second end to enhance a strength and a stability of the inter-transverse process implant between the first vertebra and the second vertebra.

11. The spinal stabilization device of claim 10, wherein the first vertebra is a relatively superior vertebra and the second vertebra is a relatively inferior vertebra of the adjacent vertebral pair.

12. The spinal stabilization device of claim 10, wherein one or more of the first end and the second end is configured to be affixed to the portion of the first vertebra that employs a fixation mechanism.

13. The spinal stabilization device of claim 10, wherein
one or more of the first end, the second end, and the middle portion includes a bone engagement feature, and
the bone engagement feature includes or more of: a fastener, a roughened surface, spikes, and hooks.

14. A method to achieve spinal fusion, the method comprising:
inserting a spinal stabilization device between an adjacent vertebral pair such that a first end of the spinal stabilization device is in contact with a first vertebra of the adjacent vertebral pair and a second end of the spinal stabilization device is in contact with a second vertebra of the adjacent vertebral pair, wherein;
the spinal stabilization device includes a first end having a first curved portion in one of a u-shape or a j-shape in a cross-sectional view and a second end having a second curved portion in one of the u-shape or the j-shape in the cross-sectional view,
the first curved portion includes a first anterior edge of a first length and a first posterior edge of a second length,
the second curved portion includes a second anterior edge of a third length and a second posterior edge of a fourth length, and
the first anterior edge includes a first cutout and the second anterior edge includes a second cutout; and
rotationally inserting the spinal stabilization device between the first vertebra and the second vertebrae such that the first curved portion straddles a first transverse process of the first vertebra and the second curved portion straddles a second transverse process of the second vertebra.

15. The method of claim 14, further comprising:
positioning the second end such that the second curved portion straddles a superior articular process of the second vertebra.

16. The method of claim 14, further comprising:
preparing a surface of one or more of the first vertebra and the second vertebra to receive the spinal stabilization device prior to insertion of the spinal stabilization device by one or more of piercing a periosteum and decorticating the surface of one or more of the first vertebra and the second vertebra prior to insertion of the spinal stabilization device.

17. The method of claim 14, further comprising inserting the spinal stabilization device via an open procedure, wherein the open procedure includes dissection and exposure to access a targeted facet joint, and removal of a portion of cartilage within the targeted facet joint.

* * * * *

UNITED STATES PATENT AND TRADEMARK OFFICE
CERTIFICATE OF CORRECTION

| | |
|---|---|
| PATENT NO. | : 9,592,083 B2 |
| APPLICATION NO. | : 14/413229 |
| DATED | : March 14, 2017 |
| INVENTOR(S) | : William Robert Walsh et al. |

It is certified that error appears in the above-identified patent and that said Letters Patent is hereby corrected as shown below:

In the Specification

In Column 1, Line 7, delete "§371" and insert -- § 371 --, therefor.

In Column 1, Line 9, delete "§119(a) and 35 U.S.C. §365(b)" and insert -- § 119(a) and 35 U.S.C. § 365(b) --, therefor.

In Column 5, Line 27, delete "end. 204" and insert -- end 204 --, therefor.

In Column 11, Line 16, delete "Additionally;" and insert -- Additionally, --, therefor.

In the Claims

In Column 28, Line 23, in Claim 13, delete "or more" and insert -- one or more --, therefor.

In Column 29, Line 1, in Claim 17, delete "comprising" and insert -- comprising: --, therefor.

Signed and Sealed this
First Day of August, 2017

Joseph Matal
*Performing the Functions and Duties of the*
*Under Secretary of Commerce for Intellectual Property and*
*Director of the United States Patent and Trademark Office*